United States Patent [19]
Suresh et al.

[11] Patent Number: 6,134,954
[45] Date of Patent: Oct. 24, 2000

[54] DEPTH SENSING INDENTATION AND METHODOLOGY FOR MECHANICAL PROPERTY MEASUREMENTS

[75] Inventors: Subra Suresh, Wellesley; Jorge Alcala, Arlington; Antonios E. Giannakopoulos, Cambridge, all of Mass.

[73] Assignee: Massachusetts Institute of Technology, Cambridge, Mass.

[21] Appl. No.: 08/632,665

[22] Filed: Apr. 15, 1996

[51] Int. Cl.[7] ........................................... G01N 3/42
[52] U.S. Cl. ................... 73/81; 702/33; 702/156
[58] Field of Search ..................... 73/81; 364/564, 364/506; 702/33, 156

[56] References Cited

U.S. PATENT DOCUMENTS

| | | |
|---|---|---|
| 1,071,430 | 8/1913 | Keen . |
| 1,125,912 | 1/1915 | Ringland et al. . |
| 1,348,897 | 8/1920 | Ringland . |

(List continued on next page.)

FOREIGN PATENT DOCUMENTS

| | | | |
|---|---|---|---|
| 607466 | 7/1994 | European Pat. Off. ............. | 73/81 |
| 1260729 | 9/1986 | U.S.S.R. .............................. | 73/81 |
| 1827579 | 7/1993 | U.S.S.R. .............................. | 73/81 |
| WO 88/00691 | 1/1988 | WIPO . | |

OTHER PUBLICATIONS

Robinson W.H. et al., "Stress–Strain Curve for Aluminum from a Continuous indentation Test", Journal of Materials Science, vol. 21, No. 10, Oct. 1977, pp. 1961–1965.

Cook, Robert F et al., "Indentation Load–Displacement Behaviour During Covnentional Hardness Testing", Journal of Hard Materials, vol. 5, 1994, pp. 179–190, Month Not Given.

Loubet, J.L. et al., "Vickers Indentation Curves of Magnesium Oxide (MgO)", Journal of Tribology, vol. 106 106. Jan. 1984, pp. 43–48.

Polvani R.S., et al. "A Dynamic Microindentation Apparatus for Materials Characterization", Journal of Test Testing and Evaluation, vol. 16, No. 1, Jan. 1988, pp. 12–16.

Database WPI, Section El. Week 9708 Derwent Publications Ltd., Class S03, AN 97–080669 XP002053699 XP002053699 & JP 08 320 284 A (Shimadzu Corp. et al.), Dec. 3, 1996, see abstract, figures.

S. V. Hainsworth, et al., "Analysis of nanoindentation load–displacement loading curves", (Aug. 1996), pp. 1987–1995, J. Mater. Res., vol. 11, No. 8.

W. C. Oliver, "An improved technique for determining hardness and elastic modulus using load and displacement sensing indentation experiments", (Jun. 1992), pp. 1564–1584, J. Mater. Res. vol. 7, No. 6.

Mortensen A. and Suresh, S. Functionally Graded Metals and Metal–Ceramic Composites: Part 1, Processing, International Materials Reviews pp. 1–62 (Sep. 1995), Plus Figs. 1–10.

Bhushan, B and Koinkar, V. Nanoindentation Hardness Measurements Using Atomic Force Microscopy, Appl. Phys. Lett 64(13) pp. 1653–1655 (Mar. 28, 1994).

(List continued on next page.)

Primary Examiner—Thomas P. Noland
Attorney, Agent, or Firm—Wolf, Greenfield & Sacks, P.C.

[57] ABSTRACT

An indentation measurement apparatus is retrofittable onto any of a variety of load-applying frames and includes a mount for mounting an indenter of any geometry (for example blunt or sharp). The arrangement is very stiff and mechanical values including Young's modulus, strain hardening exponent, yield strength, and hardness can be obtained from a single load/unload versus displacement test. A wide variety of materials can be tested using the apparatus. An optical probe can measure displacement of the indenter head relative to a sample. A new method of calculating strain hardening directly from load/displacement measurement is presented as is a new method of calculating strain hardening exponent.

18 Claims, 13 Drawing Sheets

U.S. PATENT DOCUMENTS

| | | | |
|---|---|---|---|
| 3,763,697 | 10/1973 | Sturm | 73/81 X |
| 3,805,598 | 4/1974 | Corcoran | 73/81 |
| 3,822,946 | 7/1974 | Rynkowski | 356/160 |
| 3,877,298 | 4/1975 | Narang | 73/81 |
| 3,879,982 | 4/1975 | Schmidt | 73/79 X |
| 4,023,401 | 5/1977 | Ernst | 73/81 |
| 4,104,901 | 8/1978 | Sidaway | 73/81 |
| 4,275,966 | 6/1981 | Kleesattel | 356/378 |
| 4,277,174 | 7/1981 | Kleesattel | 356/372 |
| 4,304,123 | 12/1981 | Aschinger et al. | 73/81 |
| 4,312,220 | 1/1982 | Borgersen et al. | 73/81 |
| 4,312,221 | 1/1982 | Edward et al. | 73/81 |
| 4,331,026 | 5/1982 | Howard et al. | 73/81 |
| 4,361,034 | 11/1982 | Borgersen et al. | 73/81 |
| 4,372,152 | 2/1983 | Lewis et al. | 73/81 |
| 4,383,450 | 5/1983 | Pringiers et al. | 73/790 |
| 4,463,600 | 8/1984 | Hobbs et al. | 73/81 |
| 4,530,235 | 7/1985 | Shabel | 73/81 |
| 4,535,623 | 8/1985 | Gilberto | 73/81 |
| 4,611,487 | 9/1986 | Krenn et al. | 73/81 |
| 4,621,523 | 11/1986 | Shabel et al. | 73/81 |
| 4,627,096 | 12/1986 | Grattoni et al. | 73/81 X |
| 4,653,106 | 3/1987 | Sadao et al. | 73/81 X |
| 4,667,509 | 5/1987 | Tobolski et al. | 73/83 |
| 4,671,104 | 6/1987 | Fischer | 73/81 |
| 4,691,559 | 9/1987 | Fischer | 73/81 |
| 4,699,000 | 10/1987 | Lashmore et al. | 73/81 |
| 4,820,051 | 4/1989 | Yanagisawa et al. | 356/378 |
| 4,852,397 | 8/1989 | Haggag | 73/82 |
| 4,856,326 | 8/1989 | Tsukamoto | 73/150 A |
| 4,896,339 | 1/1990 | Fukomoto | 377/19 |
| 4,945,490 | 7/1990 | Biddle, Jr. et al. | 73/81 X |
| 4,956,994 | 9/1990 | Lue | 73/81 |
| 4,984,453 | 1/1991 | Enomoto | 73/81 |
| 5,062,293 | 11/1991 | Bakirov et al. | 73/81 |
| 5,067,346 | 11/1991 | Field | 73/81 |
| 5,133,210 | 7/1992 | Lesko et al. | 73/81 |
| 5,146,779 | 9/1992 | Sugimoto et al. | 73/81 |
| 5,150,608 | 9/1992 | Mazzoleni et al. | 73/81 |
| 5,165,274 | 11/1992 | Thiercelin | 73/784 X |
| 5,177,999 | 1/1993 | Tobolski et al. | 73/82 |
| 5,193,383 | 3/1993 | Burnham et al. | 73/105 |
| 5,195,364 | 3/1993 | Dehe et al. | 73/81 |
| 5,284,049 | 2/1994 | Fukumoto | 73/82 |
| 5,309,754 | 5/1994 | Ernst | 73/81 |
| 5,355,721 | 10/1994 | Garcia | 73/82 |
| 5,359,879 | 11/1994 | Oliver et al. | 73/7 |
| 5,365,457 | 11/1994 | Madigosky | 364/506 |
| 5,483,821 | 1/1996 | Mazzoleni et al. | 73/82 |
| 5,486,924 | 1/1996 | Lacey | 356/357 |
| 5,490,416 | 2/1996 | Adler | 73/82 |

OTHER PUBLICATIONS

Soderlund, E and Rowcliffe, D "Analysis of Penetration Curves Produced by Depth–Sensing Indentation Systems" 1994 J. Hard Mater. 5, 149–177 (1994), Pub. Month Not Given.

National Institute of Standards and Technology (NIST) Special Publication 896: "Conference Proceedings: International Workshop on Instrumental Indentation", San Diego, CA, Apr. 22–23, 1995, pp. iii–vii, pp. 1–9, and p. 41.

J.S. Field and M.V. Swain, "Determining the mechanical properties of small volumes of material from submicrometer spherical indentations", J. Mater. Res., vol. 10, No. 1, Jan. 1995, pp. 101–112.

P.–Larson and A.E. Giannakopoulos, E. Söderlund and D.J. Rowcliffe, and R. Vestergaard, "Analysis Analysis of Berkovich Indentation", Int. J. Solids Structures, vol. 33, No. 2, 1996, pp. 221–248.

R. Hill, F.R.S., B. Storakers and A.B. Zdunek, "A theoretical study of the Brinell hardness test", Proc. Ro. Soc. Lond. vol. A423 (1989), pp. 301–330, Pub. Month Not Given.

A.E. Giannakopoulos, P.–L. Larsson and R. Vestergaard, "Analysis of Vickers Indentation", Int. J. Solids Structures, vol. 31, No. 19 (1994), pp. 2679–2708, Pub. Month Not Given.

DEPTH SENSING INDENTATION AND METHODOLOGY FOR MECHANICAL PROPERTY MEASUREMENTS

FIELD OF THE INVENTION

The present invention relates generally to measuring mechanical properties of materials, and more particularly to indentation testing with the purpose of measuring such properties as hardness, yield strength, strain hardening exponent, and Young's modulus.

BACKGROUND OF THE INVENTION

The testing of mechanical properties of materials is a well-studied art. Standard tests exist for measuring mechanical properties such as Young's modulus, strain hardening exponent, yield strength, hardness, and the like, and many materials have been carefully characterized in terms of mechanical properties. One set of techniques for determining mechanical properties in materials involve tests in the macro regime in which, for example, a sample of material is stretched and its overall mechanical response inferred in terms of stress and deformation. These and other techniques have served, and continue to serve, an important role in determining critical mechanical properties so that careful processing and selection of materials for use in a variety of industrial settings can be made.

The above-described techniques, however, typically require large samples of material and generally are destructive of those samples. There is an increasing need in the field of materials science for analysis of small-scale samples in a manner that can be essentially non-destructive. The increasing rate of miniaturization in the semiconductor field, increasing interest in thin coatings for optical, electronic, magnetic, and mechanical devices, and increasing use of functionally-graded materials have led to a need for in situ testing of mechanical properties in small-scale structures. Additionally, there is interest in probing properties of individual phases, grain boundaries, and interfaces between phases and properties of novel materials such as nanocrystalline materials, or laminated or fibrous composites.

Indentation testing has developed as a viable technique for determining certain properties in a variety of materials at a very small scale, essentially non-destructively. Indentation testing typically involves placing a sample to be tested on a stage and applying a load to a surface of the sample via an indenter so as to slightly deform or penetrate the surface, followed by removal of the load. Several techniques can be employed to derive certain properties of the material from characteristics of the interaction of the indenter with the material. One set of techniques involves measuring an area of indentation during or after indentation, for example, optically, refractively, via surface profilometry, etc. U.S. Pat. Nos. 4,627,096 (Grattoni, et al.), 4,945,490 (Biddle, Jr. et al.), 5,284,049 (Fukumoto), 5,355,721 (Las Navas Garcia), 5,483,621 (Mazzoleni), 5,486,924 (Lacey), 4,852,397 (Haggag), 5,490,416 (Adler), 3,822,946 (Rynkowski), and others follow this procedure. For example, the measured area of indentation can be used to determine a simple "flow" or hardness value for the material, which is defined as the load applied divided by the projected area of the indentation. Or, the dimension of any cracks formed in the sample surface can be measured to determine the toughness of the material. Alternatively, the depth of penetration of the indenter as a function of applied load can be measured, and calculations performed to estimate roughly some mechanical properties. As discussed below, these techniques, in the prior art, have disadvantages.

Various shapes of indenters, for example spherical, cone-shaped, and pyramidal geometries can be used in indentation testing. Sharp indenters (e.g., cone-shaped and pyramidal) can be used in conventional tests to apply a load to a sample surface to form an imprint, or until the surface cracks, followed by measurement of the area of imprint or determination of the crack length to measure hardness or toughness, respectively. One piece of indentation testing equipment utilizing a sharp indenter at ultra low loads is sold by Nano Instruments, Inc. as the Nanoindenter™ indentation tester. The Nanoindenter™ is a relatively complex, self-contained unit including an indenter system, a sharp indenter, a light optical microscope, a moveable x-y table, and a computer. Analysis of load/depth curves with loads of less than one Newton and displacement of less than one $\mu m$ using a three-sided pyramidal indenter is most typically carried out.

Blunt indenters, for example those having a surface contacting the sample surface that is spherical, are advantageous for use in indentation testing under certain circumstances for several reasons. First, less sample-destructive analyses often can be carried out. However, with blunt (spherical) indenters, sensitivity problems are maximized since displacement of the sensor into the sample surface, at a particular applied load, is less than displacement with a sharp indenter. This is especially problematic in measuring very soft materials. Spherical indenters have, therefore, found most use in techniques in which load is applied to a sample surface and the diameter of the indentation formed thereby is measured using, for example, optical means.

U.S. Pat. No. 4,820,051 (Yanagisawa, et al.) discloses self-contained apparatus for measurement of the hardness of materials. A load is applied to a sample via a sharp indenter (having a tip with a radius of curvature between 0.01 and 0.1 $\mu m$), and the displacement of the indenter relative to the sample is determined. An optical sensing mechanism determines the penetration depth of the indenter. Yanagisawa, et al. measure load/displacement values only during application of the load, with a self-contained unit, and measure only hardness of the material. Yanagisawa, et al. measure penetration and, with knowledge of the indenter geometry and assuming that no pile-up or sinking-in of the material at the contact perimeter occurs (which is known to be a factor that must be taken into account for accurate measurement), appear to calculate what the area of the indentation would be without sinking-in or pile-up, to measure hardness. Measurements are made in a load range of less than one Newton.

Gattoni, et al. (U.S. Pat. No. 4,627,096) recognize that sinking-in during indentation testing should be taken into account when measuring hardness of a sample (see, e.g., FIGS. 1 and 4). Therefore, Gattoni, et al. illuminate the sample carrying the impression and optical processing equipment is used to determine the contact area between the indenter and the sample.

U.S. Pat. No. 4,699,000 (Lashmore, et al. describes self-contained apparatus and methods for determining hardness. Displacement of the indenter into the sample as a function of time, using sharp indenter geometries, is made and a load versus displacement curve is thereby derived. Lashmore, et al., measure penetration and, with knowledge of the indenter geometry and assuming no pile-up or sinking-in, calculate the area of the indentation (column 5, lines 5–43) to measure hardness using a self-contained unit. The displacement sensor of Lashmore, et al. is quite removed spatially from the indenter (FIGS. 2, 3). Lashmore, et al. state that modulus, yield strength, impact, hardness, creep and fatigue also can be determined. No indication, however, is given as to how to go about determining these properties or whether, using the described techniques, accurate determination of these properties can be made.

U.S. Pat. No. 5,133,210 (Lesko, et al.) exploits thermal expansion in applying a load to a sample surface via a spherical indenter. Various measurements of load versus penetration (displacement) are made and theories are presented as to how various mechanical properties can be derived. However, Lesko, et al. do not take into account sinking-in or pile-up of material at the contact perimeter. Additionally, it appears from FIG. 5 of Lesko and theoretical analysis (Col. 5, lines 35–39 and Col. 4, lines 50–53) of Lesko, et al., that the assumption is made that the plastic regime of the load/displacement curve is linear. This assumption ignores the known non-linearity of the strain hardening exponent. Lesko, et al. do not show experimental data supporting the evaluation of Young's modulus from a load/displacement curve. Moreover, the displacement sensor is quite removed spatially from the indenter (FIG. 3 of Lesko). Only ball indenters, and self-contained units, are described. Measurements are made in the 1000 Newton range. It is unclear how the methodology of Lesko, et al. would be applied to measurement at low loads.

U.S. Pat. No. 5,490,416 (Adler) describes indentation of surfaces of materials using a spherical indenter to determine hardness. Load is applied to a sample via the indenter, but no load/depth relationship is experimentally obtained. In an effort to accurately take into account sinking-in and pile-up of material at the contact perimeter, a relatively time-consuming and labor-intensive process is carried out involving multiple indentation tests where the profile of the indentation is traced after each test with a surface analyzer to determine the depth and diameter of the indentation. Adler mentions that other devices may be used to measure the depth while load is being applied. However, no specific experimental arrangements are described in detail. No indication is given that any mechanical properties are measured directly from any portion of a load/displacement curve. Additionally, the theoretical framework relied upon assumes only plastic material properties.

U.S. Pat. No. 4,852,397 (Haggag) describes a self-contained field indentation microprobe that measures load and penetration depth data during both loading and unloading cycles to determine flow properties and fracture toughness of a structure. The described apparatus is specifically designed for use in the field to determine mechanical characteristics of large samples, for example, a damaged pressure vessel or tank car. Haggag uses ultrasonic analyzers to measure thickness, internal presence of cracks, and pile-up around indentation after testing, and uses a video camera to measure an indentation formed from load applied with a spherical indenter. Haggag states that the slope of the unloading portion of a load/displacement curve can be used as a measure of elastic properties, but nowhere does Haggag describe derivatization of area of indentation from a load/displacement measurement. Measurement in the kiloNewton range and above is made.

Accurate determination of the area of an indentation formed during indentation testing, especially during loading, can be critical to accurate determination of several mechanical properties of a sample. One drawback of prior art indentation testing techniques is that determination of the area of the indentation formed while load is applied either is not made precisely, or requires relatively complicated apparatus. Prior indentation testing typically involves either forming an indentation, removing the indenter, and observing the size of the imprint with, for example, an optical microscope, profilometer, or the like (which adds a step to analysis and cannot account for elastic rebound of the material after unloading, which typically is significant), or indentation depth is measured and the area of indentation calculated with mere knowledge of the geometry of the indenter (which is an approximation that fails to take into account material pile-up or sinking-in, which is almost always relevant and affects the evaluation of mechanical properties), or involves complicated optical apparatus (such as that used by Grattoni, et al., U.S. Pat. No. 4,627,096).

Additionally, most known techniques cannot accurately determine properties of a sample in the elastic and plastic regimes within a single test. Moreover, most prior art techniques involve load/displacement analysis either at very low loads (in the nano regime), or at very high loads (tens or hundreds of kilograms), but do not provide the capability of sampling load/displacement characteristics of a variety of materials over a very wide range of loads to determine local as well as bulk properties.

Therefore, it is an object of the invention to provide apparatus and methods for indentation testing that allows for simple, relatively uncomplicated and inexpensive, and accurate measurement of a variety of mechanical properties. It is another object of the invention to provide indentation testing apparatus that can determine several mechanical properties in a single test or series of tests accurately, and reproducibly. It is another object of the invention to provide indentation testing apparatus that can sample materials accurately at very low loads, but is also capable of operating over a wide range of loads so that mechanical characterization of a material in the bulk as well as local regime can be carried out. It is another object of the invention to provide such apparatus in which indenters of a variety of shapes and sizes can be used. It is another object of the invention to provide a methodology and corresponding theoretical framework directly coupled to in situ load/displacement measurement using a variety of indenter shapes and sizes to derive mechanical properties.

SUMMARY OF THE INVENTION

The present invention provides apparatus and methodology for measuring mechanical properties of materials via indentation testing. According to one aspect, the invention involves deriving an accurate area of contact between an indenter and a sample during indentation testing, from the load/depth relationship resulting from the test. The load/depth relationship is included in data provided from an indentation test in which load is applied to a surface of a sample of material with an indenter to cause the indenter to penetrate the surface to a depth. The load/depth relationship is defined by depth of penetration of the indenter into the sample as a function of load applied to the sample via the indenter. The area of contact is derived from the load/depth relationship directly, that is, without observing the area of contact between the indenter and the sample during or after penetration. The area derived thereby includes area of contact due to pile-up of sample material around the indenter, or takes into account sinking-in of the material. The providing step can involve providing earlier-recorded data that has been stored electronically, for example in a computer or on a computer recording medium such as a disk, can involve providing data from a remote testing site electronically, can involve analyzing a plotted load/depth relationship, or the like. Additionally, the providing step can involve measuring the data locally (i.e. at the same location at which the area of contact is derived, and using apparatus in electronic communication with the deriving apparatus) by applying to the sample a load via an indenter and measuring penetration of the indenter into the sample as a function of applied load. The apparatus can include a stage for mounting a sample, an indenter, a load cell, and a sensor constructed and arranged to determine displacement of the indenter relative to a sample on the stage.

According to another embodiment, the invention involves using indentation testing apparatus to probe a sample of material having an elastic strain limit $\sigma_y/E$ of less than about 0.05 with a blunt indenter, and deriving Young's modulus of the material from the initial loading portion of the load/depth relationship obtained during probing. The load/depth relationship is established by measuring penetration of the indenter into the sample as a function of applied load. According to one embodiment, the radius of curvature of the blunt indenter is less than about 6 mm. The method can involve also deriving yield strength and/or strain hardening exponent from the load/depth relationship. Young's modulus also can be derived from the initial unloading portion of the load/depth relationship.

According to another embodiment, the invention involves probing a sample of material that has a stress-strain curve with a non-linear slope with an indenter, measuring penetration as a function of applied load, and deriving strain hardening exponent from the loading portion of the load/depth relationship.

According to another embodiment, the invention involves probing a sample of material with a blunt indenter to obtain a load/depth relationship, and deriving strain hardening exponent of the material from the load/depth relationship.

The invention also provides a method that involves deriving one of yield strength or strain hardening exponent of a sample of material from a load/depth relationship obtained via an indentation test using a sharp indenter.

According to another embodiment of the invention, Young's modulus arid at least one of yield strength, strain hardening exponent, and hardness of material is derived from a single load/depth relationship in an indentation test.

One aspect of the invention involves deriving the area of contact between the indenter and sample from the load/depth relationship of any or all of the above-described methods, and using the area of contact so derived to derive Young's modulus, yield strength, tensile strength, strain hardening exponent, and/or hardness. The area of contact includes the area due to pile-up of sample material at the periphery of contact between the indenter and the material, or takes into account sinking-in of the material due to indentation.

Any of the above-described methods can involve immobilizing a sample of material on a stage prior to or during an indentation testing. According to one embodiment, the invention provides a method of indentation testing involving immobilizing a sample on a stage, applying a load of greater than at least about one Newton via an indenter, and determining a load/depth relationship of the material. One way of immobilizing the sample can involve securing the sample to the stage by a clamp or bracket or other device that applies a force to the material having a component in the direction of the stage. The sample can be secured to the stage after load is applied to the sample via the indenter. This can involve applying load via an indenter and, at any degree of applied load, securing the sample by, for example, tightening a clamp that clamps the sample to the stage. One embodiment involves securing the sample to the stage by, for example, tightening a clamp holding the sample on the stage, at maximum load. This can be particularly beneficial in measuring properties during unloading.

According to another aspect, the invention provides indentation testing apparatus that is easily retrofittable into a separate load-applying frame, that is, a load-applying frame that is not necessarily built specifically for indentation testing. According to one embodiment, the apparatus includes a stage for mounting a sample, an indenter mount, a load cell, and a displacement sensor constructed and arranged to determine displacement of the indenter mount relative to the sample. The apparatus is readily mountable in and removable from a load-applying frame using common fasteners. According to one embodiment, the displacement sensor is positioned within about 5 cm of a point at which an indenter carried by the indenter mount contacts a surface of a sample carried by the stage. The indenter mount can be one constructed and arranged to mount a spherical indenter and, according to one embodiment, the displacement sensor is positioned within a distance of about 20 times the diameter of the indenter from the point at which a spherical indenter carried by the indenter mount contacts a surface of a sample mounted on the stage. When a spherical or other blunt indenter is employed, an indenter mount of the invention can be used that has a surface that contacts the blunt indenter mounted therein that is harder and stiffer than steel. According to one embodiment, that surface is at least twice as hard and stiff as the sample tested.

Another embodiment of the invention involves particularly accurate retrofittable indentation testing apparatus. According to this embodiment, apparatus is provided including a stage, and indenter mount, a load cell, a displacement sensor, and is readily mountable in and removable from a load-applying frame using common fasteners. The apparatus is capable of determining a physical characteristic, from a load/depth relationship obtained by applying load to a sample on the stage via an indenter carried by the indenter mount and measuring penetration of the indenter into the sample. The physical characteristic can be one of Young's modulus, yield strength, tensile strength, strain hardening exponent, and hardness, and is determined with less than about 20% error.

Other advantages, novel features, and objects of the invention will become apparent from the following detailed description of the invention when considered in conjunction with the accompanying drawings.

Figure 1:
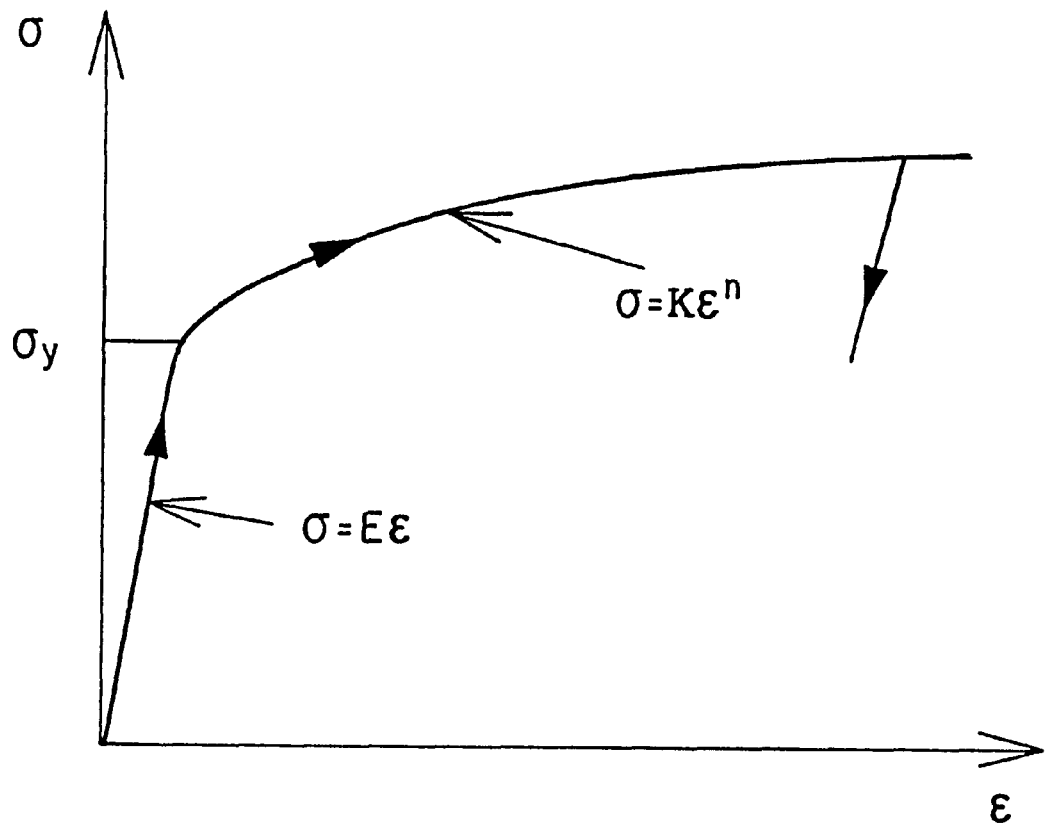
FIG. 1 is a schematic of a typical uniaxial true stress-strain curve representative of knowledge in the art.

NOMENCLATURE $a_{max}$: maximum contact radius of a spherical indenter at load
$A_{max}$: contact area of an indenter at maximum load
c: parameter that accounts for sinking-in or pile-up at the contact perimeter of a spherical indenter
C: elasto-plastic stiffness of pyramidal indenters
C*: coefficient to account for the shape of pyramidal indenters
O: diameter of a spherical indenter
$D_p$: minimum diameter of a spherical indenter to avoid plastic deformation of a sample under load less than the resolution of the system
$D_c$: maximum diameter of a spherical indenter to avoid radial cracking of a sample under maximum indentation load
$D_c'$: minimum diameter of a spherical indenter to avoid ring cracking of a sample under maximum indentation load
E: Young's modulus of sample
E': Young's modulus of a spherical indenter
E*: combined effective Young's modulus (indenter and sample)
h: measured depth of an indenter relative to the surface of a sample (penetration; displacement)
$h_{max}$: measured maximum indentation depth (penetration; displacement)
$h_{min}$: depth resolution of the system
$h_{min}'$: elastic depth corresponding to the load resolution of the system
$h_m$: recommended maximum indentation depth for characterization of a layer or a grain of the sample
$h_r$: residual indentation depth after complete unloading
$h_s$: total size of a diamond pyramid indenter
$h_y$: maximum elastic depth of a spherical indenter
H: secant elasto-plastic modulus at 30% plastic strain
K: characteristic stress for the power law elasto-plastic behavior
$K_c$: critical stress intensity factor of a sample
n: uniaxial compression strain hardening exponent of sample
$P_{av}$: Mayer's hardness or average contact pressure at maximum load
P: load applied to sample via an indenter
$P_m$: maximum load of a sharp indenter to avoid radial cracking at the corners of a pyramid indentation
$P_{max}$: maximum load applied to sample via an indenter
$P_{min}$: load resolution of the system
$P_y$: maximum elastic force of a spherical indenter $$\left.\frac{dP}{dh}\right|_{h_{max}}$$

initial slope, at maximum load, of the load/depth unloading curve
X: distance between the displacement sensor and the axis of an indenter
G: 22° for Vickers and 24.7° for Berkovich pyramid indenters
$\epsilon$: true strain in uniaxial compression
$\epsilon_{max}$: maximum characteristic plastic strain for a spherical indenter
$\nu$: Poisson ratio of sample
$\nu'$: Poisson ratio of a spherical indenter
$\sigma$: true stress in uniaxial compression
$\sigma_u$: uniaxial, compressive, true stress at 30% plastic strain
$\sigma_y$: yield strength in uniaxial compression of sample
$\sigma_y'$: yield or failure strength of the spherical indenter
$\Phi$: angle of deviation of normality of an indenter to sample surface

DETAILED DESCRIPTION OF THE INVENTION

The present invention provides indentation testing methods and apparatus for deriving information on mechanical properties of a sample of material without the requirement of observation of the imprint formed. The information is derived from data provided from an indentation test, which data can be obtained by probing a sample of material and deriving the information, probing a sample of material, storing the data electronically, and providing the data at a later time and/or different location and then deriving the information. The area of the imprint is obtained directly from load/displacement measurement, and accurately takes into account pile-up and sinking-in of material during indentation. The apparatus is constructed to accurately measure displacement of an indenter during both loading and unloading of the indenter, even at relatively low loads, and can probe a sample using virtually any indenter geometry. Several mechanical properties can be determined in a single load/unload cycle and accuracy of determination of several properties can be assessed by comparison between analyses using different indenter geometries.

As mentioned, observation of an imprint formed during indentation is not required. This means that observing the imprint formed during indentation, for example via optical apparatus arranged to provide a visual signal of the imprint through the indenter, or apparatus designed to determine an electromagnetic radiation signal reflected or refracted from the imprint, and the like is not required. Additionally, removal of the indenter and observation of the resulting imprint optically, via profiletry, and the like is not required. The invention provides methodology for derivation of mechanical properties directly from the displacement of an indenter relative to a sample as a function of applied load.

Obviating the need for observation of the imprint during or after penetration is a significant improvement.

Indentation depth/load relations are measured in situ with the apparatus of the invention by monitoring the penetration of an indenter into a polished specimen over a range of applied loads. The determination of these relations using blunt (spherical or rounded tip) and sharp indenters (such as those having cone or pyramidal geometries, commonly referred to as Rockwell, Vickers or Berkovich indenters) enables the determination of fundamental mechanical properties such as Young's modulus (E), strain hardening exponent (n), yield strength ($\sigma_y$), and microhardness ($P_{av}$). As is well known in the art, these properties can be obtained from certain data revealed by a stress-strain curve of a sample, which can be obtained using standard macro scale tests. A typical stress-strain curve is illustrated in FIG. 1. One major purpose of the present invention is to improve techniques for obtaining such properties using indentation testing.

A wide variety of samples such as metals, oxides, carbides, ceramics, glasses, polymers, composites, layered solids such as surface coatings, and similar materials can be measured. The methodology and apparatus of the invention focuses on isotropic, homogeneous, elastic and elasto-plastic materials at room temperature. According to one feature, isotropic strain hardening can be determined in elasto-plastic materials.

In addition to many research-type applications, the present apparatus and methodology can be used in routine industrial practice in inspection of materials, potentially non-destructively, such as metallurgical operation on alloys (e.g., quenching, tempering, nitriding, case-hardening, and annealing) as well as to study variation of chemical composition (e.g., through diffusion). Such examinations on small components make the inventive process quantitative.

The invention involves, according to preferred embodiments, determination of Young's modulus (E) from the unloading portion of a load/displacement curve where a sharp indenter is used and/or from the initial portion of the load/depth measurement as well as from unloading using a spherical indenter; strain hardening exponent (n) from the loading portion of the load/displacement curve in a load range where the material behavior is non-linear using a spherical or sharp indenter; and yield strength $\sigma_y$ from load/depth data as measured with a spherical indenter. Yield strength data so obtained can be checked by the loading portion of a sharp indentation test. The invention also involves combination, or comparison, of any of these processes with known measurement techniques.

Figure 2:
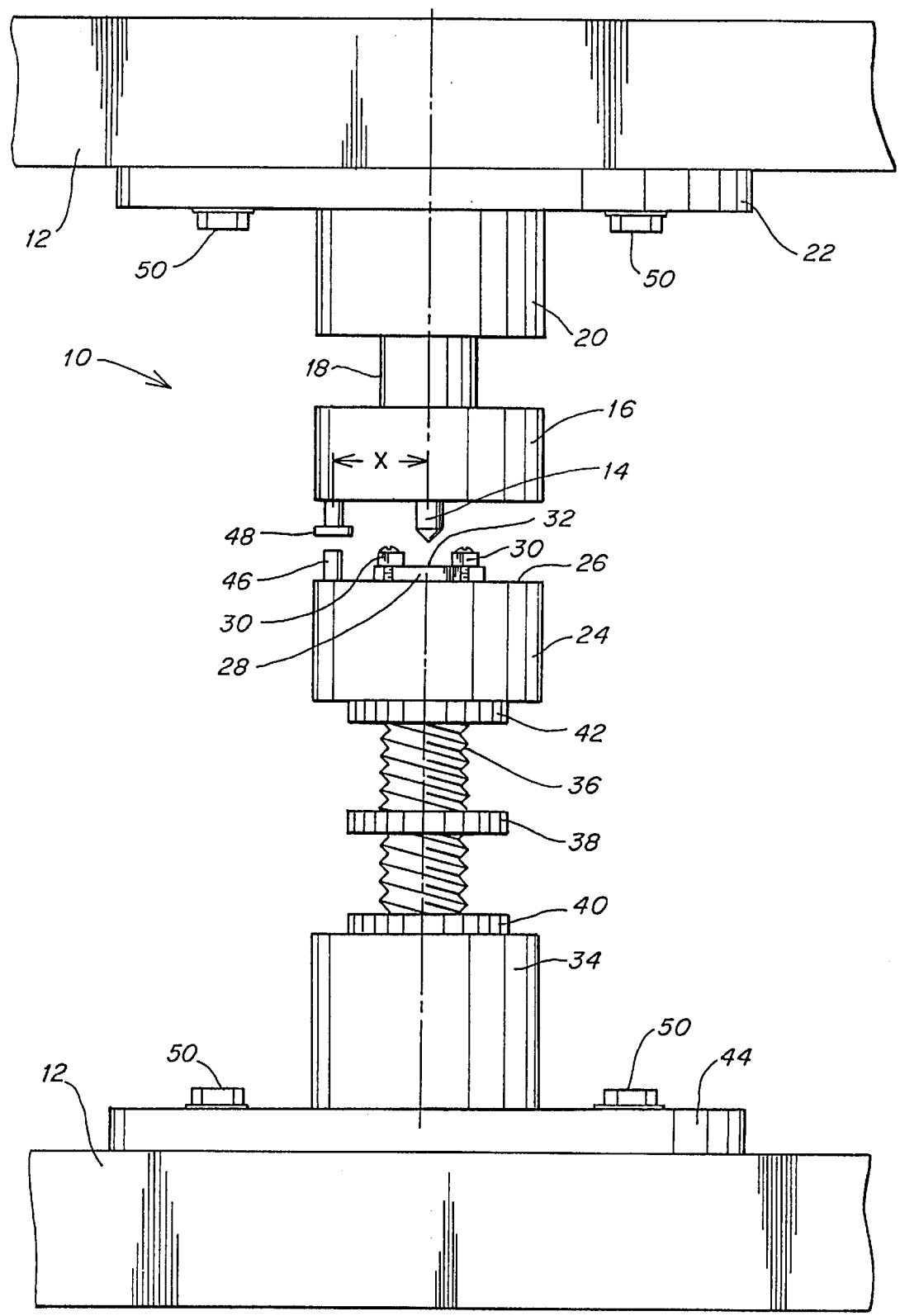
FIG. 2 illustrates schematically indentation testing apparatus of the invention.

Referring to FIG. 2, indentation testing apparatus 10 of the invention is schematically illustrated as mounted in an existing laboratory load-applying frame 12. According to a preferred embodiment, apparatus 10 is axisymmetric, that is, symmetric about the axis of loading. Apparatus 10 includes an upper, indenter-carrying portion and a lower, sample-carrying portion. The upper portion includes an indenter assembly 14 mounted securely on an indenter mount 16 which is fastened to a load cell 18, which is in turn fastened to an upper mount 20 including an upper flange 22 adapted to be secured to the load-applying frame. The lower, sample-carrying portion includes a fixture 24, a top, or stage surface 26 of which defines a stage upon which a sample 28 is positioned for testing, and against which the sample can be securely held with one or more clamps, or brackets 30. The apparatus is arranged such that the indenter is positioned above a top surface 32 of sample 28. Top surface 32 is desirably polished prior to analysis.

Fixture 24 is secured to a base support 34 by, for example, a threaded adjusting mount 36 that threads into fixture 24 and/or base support 34. Adjusting mount 36 is preferred, but not necessary. Fixture 24 can be secured directly to (or be integral with) base support 34. As illustrated, a rotation grip 38 allows rotation of threaded adjusting mount 36, a lock nut 40 threaded on mount 36 can secure threaded adjusting mount 36 via frictional engagement with base support 34, and a lock nut 42 threaded on mount 36 can secure threaded adjusting mount 36 via frictional engagement with fixture 24. This arrangement allows for rotation of threaded adjusting mount 36 about a vertical axis to adjust the distance between indenter assembly 14 and sample surface 32, and independent adjustment of the rotational orientation of stage surface 26 and sample 28 so that sensor 46 and mirror 48 (discussed below) can be aligned. As discussed below, a displacement sensor can also be adjusted independently. Base support 34 includes a lower flange 44 adapted to be secured to load-applying frame 12.

A displacement sensor 46 is provided to measure displacement of an indenter carried by indenter apparatus 14 relative to a surface 32 of sample 28 that is probed by the indenter. Preferably, a displacement sensor 46 is associated with fixture 24 or indenter mount 16 and, as illustrated, the sensor is an optical sensor mounted on stage surface 26, and a corresponding mirror 48 is mounted on indenter mount 16. Optical displacement sensors, for example a combination photonic probe and photonic sensor sold by Photonics, Inc, are known. Equivalent displacement sensors of similar resolution are acceptable according to this embodiment. Mirror 48 is positioned so as to reflect light emitted by sensor 46 back to the sensor. In this manner the sensor can determine the displacement of the indenter relative to surface 32 of sample 28. The sensor operates via a standard technique by which the variation of intensity between the emitted and received light is used to measure the relative motion between the probe and mirror 48 (thus displacement of the indenter relative to surface 32 of sample 28).

The vertical position of mirror 48 relative to indenter mount 16 can be adjusted, for example via a threaded coupling and lock nut, or via slidable engagement and screw (not shown). In this manner the position of mirror 48 relative to optical sensor 46 is adjustable to achieve optimal distance therebetween for measurement of penetration into the sample. Additionally, the distance between the indenter assembly 14 and surface 32 of sample 28 can be decreased at a controlled rate by adjusting the loading frame within which the system is positioned (described more fully below).

When a load is applied to surface 32 of sample 28 via the indenter, the applied load is measured with load cell 18, and in conjunction with optical sensor 46, a load/displacement curve can be obtained, both upon loading and unloading of the sample. The optical sensor 46 measures the depth of penetration of the indenter of indenter assembly 14 into surface 32 of sample 28 with an accuracy of at least about 0.5 $\mu$m, more preferably at least about 0.2 $\mu$m, and most preferably at least about 0.1 $\mu$m. The load cell 18 has a resolution of approximately at least about 0.1 N. more preferably at least about 0.05 N, and more preferably at least about 0.02 N. Load cell 18 can apply any of a wide variety of loads, and the apparatus is preferably suited for conducting indentation tests in the region of from about 0.5 N to about 500 N.

The diameter of the indentation made is preferably less than about 1/5 of the smallest diameter of the specimen (lateral dimension or height), in homogeneous materials. For layered materials, indentation depth should be less than about one-tenth of the thickness of the layer sampled to obtain properties of the layer, or greater than the thickness to obtain properties of the substrate.

One aspect of the invention involves particularly accurate measurement via a combination of stiffness and arrangement of the overall indenter apparatus. According to one embodiment, a distance X as illustrated in FIG. 2 between optical sensor 46 and the indenter is minimized (under the constraint of specimen dimension). Minimizing the distance X between optical sensor 46 and the indenter minimizes the effect of any deviation from normality or misalignment of load train, between the movement of the indenter relative to sample 28, on the accuracy of measurement. This, in combination with the stiffness of the apparatus, contributes to heightened accuracy. It has been found that, preferably, the distance X is less than about 2 centimeters, more preferably less than about 1.5 centimeters, and more preferably still less than about 1 centimeter. Of course, dimension X must be great enough to accommodate a sample of relatively large lateral dimension, and may be larger than these preferred ranges. With stiff apparatus, greater dimensions can be accommodated, and this is taken into account below.

According to one embodiment, the arrangement of apparatus 10 is such that the normality of movement of the indenter relative to surface 26 of fixture 24 is within a prescribed range. As discussed, any deviation from normality is minimized by close proximity of optical sensor 46 and the indenter. Deviation from normality of movement of the indenter relative to surface 26 can be quantified in relation to this distance X. Preferably, if the deviation of normality of movement of the indenter relative to surface 26 is assigned an angle value F, sin F will be greater than or equal to 0.05 $\mu$ms divided by distance X between optical sensor 46 and the indenter. More preferably, sin F will be greater than or equal to 0.03 $\mu$ms/X, and most preferably greater than about 0.015 $\mu$ms/X.

As discussed above, the invention provides very stiff apparatus, which is particularly advantageous. Additionally, the apparatus is designed as a unit that is retrofittable into essentially any load-applying laboratory apparatus. As illustrated in FIG. 2, flange 22 of upper mount 20 and flange 44 of base support 34 each are bolted to frame 12 (described below) with bolts 50 that each pass through their respective flange and are threaded into frame 12. This is described more fully below with reference to FIG. 7.

It has been found that where threaded connections are made between each portion of apparatus 10 that defines a separate component, that is, each component that is removable from an adjacent component using routine tools without cutting (for example upper mount 20 and frame 12, base support 34 and frame 12, threaded adjusting mount 36 and base support 34, threaded adjusting mount 36 and fixture 24, bracket 30 and fixture 24, indenter mount 16 and load cell 18, etc.), stiffness of the apparatus within preferred ranges can be achieved. In particular, apparatus having a stiffness great enough for accurate measurement of materials as hard as ceramics, using a blunt indenter, in particular one having no portion that contacts the material having a radius of curvature of less than about 2 $\mu$m, is possible.

Preferably, all components of apparatus 10 (with the exception of, e.g., mirror 48, displacement sensor 46, and the indenter) are made of stainless steel.

Figure 3:
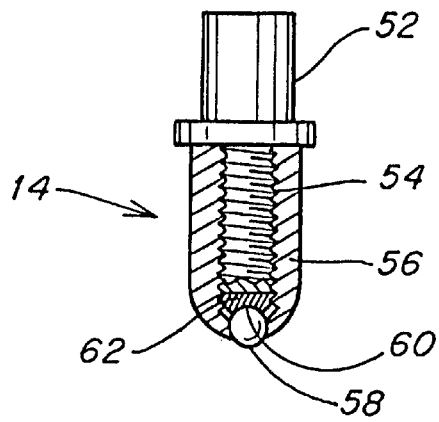
FIG. 3 illustrates schematically a mount for a spherical indenter.

Referring to FIG. 3, an indenter apparatus 14 for mounting a variety of indenters is illustrated schematically in partial cross-section. Apparatus 14 includes a portion 52 adapted to be secured to indenter mount 16. Portion 52 can include threads, and can be threaded into mount 16, fit slidably into mount 16 and be secured therein with a lock bolt (not shown), or the like. Preferably, connection between indenter apparatus 14 and mount 16 is made via threaded coupling which is meant to include threading engagement between portion 52 and mount 16, or sliding engagement secured by a threaded locking mechanism. Apparatus 14 includes a core 54 that is integral with portion 52, or securely fastened thereto preferably threadingly. A threaded clamp 56 is constructed and arranged to hold a spherical indenter 58 at its distal end. Clamp 56 threadingly engages core 54, to which pressure is applied through load cell 18 via indenter mount 16. Core 54 includes a bottom surface 60 that engages a top surface of the indenter. Thus, when clamp 56 is fastened securely to the threaded core 54 such that the indenter is positioned firmly adjacent bottom surface 60 of core 54, any slack between the indenter and the load cell is minimized.

According to one preferred aspect of the invention, especially where a particularly hard sample is to be analyzed, a lower portion 62 of core 54 including surface 60 that impinges upon the indenter is particularly hard. Preferably, portion 62 is at least 1.5 times as hard as the sample to be analyzed, more preferably 1.75 times as hard, more preferably at least twice as hard, and most preferably at least about 3 times as hard. Selection according to these criteria avoids indentation of core 54 with indenter 58 ("double indentation") which can lead to inaccuracy in penetration measurement. Portion 62 can be made of, for example, tungsten carbide where remaining portions of the assembly 14 are made of steel (in addition to, or with the exception of, indenter 58 which can comprise any indenter material). The thickness of portion 62, that is, the depth into core 54 in a direction away from indenter 58 that is defined by the particularly hard material 62, is at least about 0.5 mm, more preferably, at least about 1.0 mm. Adequate stiffness typically can be achieved within these ranges since the force applied by the indenter against the lower surface of portion 62 of core 54 during indentation is rapidly diffused laterally with increasing depth into core 54.

It has been determined, in accordance with the invention, that accuracy can be maximized by cleaning indenter 58 and surface 60 of core 54 with, for example, alcohol or acetone prior to assembly of indenter apparatus 14 and testing. Dirt particles between indenter 58 and surface 60 can act as indenters of indenter 58 and surface 60. Additionally, it can be advantageous similarly to clean stage surface 26 and the surface of sample 28 that is placed adjacent the stage surface.

Figure 4:
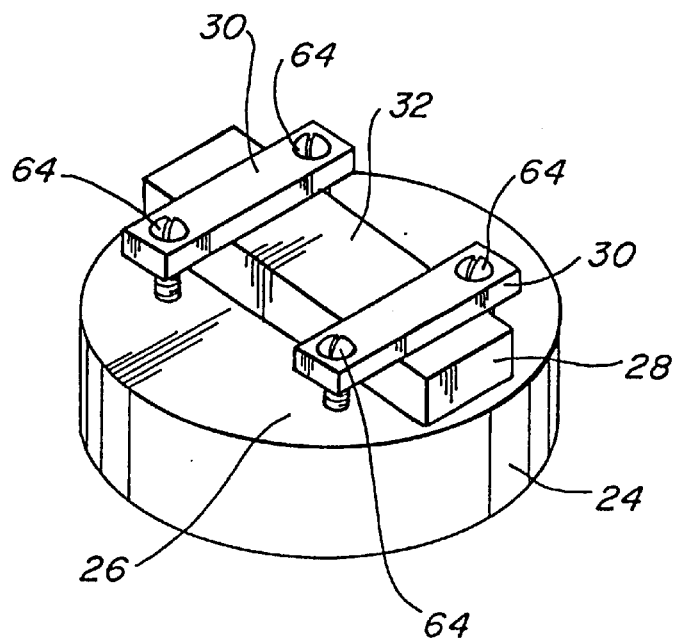
FIG. 4 illustrates schematically apparatus for securing a sample to a stage.

FIG. 4 illustrates more particularly, in perspective view, a mechanism for immobilizing a sample 28 on the upper surface 26 of fixture 24, that is, mounting a sample 28 on the upper (stage) surface 26 of fixture 24 securely in accordance with the invention. As illustrated, according to a preferred embodiment brackets 30 are placed across top surface 32 of sample 28, and each includes a portion that is securely fastenable to fixture 24 via, for example, bolts 64 as illustrated. Where sample 28 is secured tightly to fixture 24 in accordance with the invention, any slack between sample 28 and the top (stage) surface 26 of fixture 24 is minimized or eliminated. Preferably, the surface of the sample that contacts the stage surface is "lapped" prior to mounting to minimize micromotion. It is another feature of this aspect of the invention that 15 brackets 30 will prevent movement of the sample 28 away from stage surface 26 during unloading, where the sample tends to adhere to the indenter. It is another feature that any movement laterally of sample 28 relative to stage surface 26 is minimized or eliminated. One or more of these features, especially minimization of slack during loading and secure downward fastening during unloading, eliminates or minimizes any erroneous reflection of such movement in the load/displacement curve obtained via indenter probing of the sample. In many cases the brackets will affect displacement on unloading to a much greater extent than on loading. Those of ordinary skill will recognize a variety of mechanisms for securing sample 28 to fixture 24 in a manner that applies significant downward force on sample 28 in the direction of fixture 24, and these and other mechanisms are intended to be embraced by the invention. The invention resides in the recognition of error in measurement that can result from lack of such secure fastening, and the provision of a securing mechanism.

Brackets 30 can be positioned as close as feasible to the portion of surface 32 of sample 28 that is to be contacted by the indenter. Preferably, at least one bracket is spaced, and more preferably two are spaced, no more than 2 cm from the point of contact between the indenter and surface 32, more preferably no more than 1.5 cm, and more preferably still no more than 1 cm therefrom.

One aspect of the invention allows for urging sample 28 against stage surface 26 during application of load, via an indenter, to surface 32 of sample 28. For example, load can be applied to the sample via the indenter and brackets 30 tightened against sample 28 at any point during the application of load. According to one embodiment, brackets 30 are tightened against sample 28 at maximum indenter applied load. This can result in particularly precise measurement during unloading.

Another technique for immobilizing sample 28 on stage surface 26 is by adhering the sample to the stage surface. This can be done by coating stage surface 26, or the bottom surface of sample 28, with an adhesive prior to placing the sample on the stage surface, optionally urging the sample against the stage surface via, for example, clamping, and allowing the adhesive to adhere the sample to the stage surface. According to a more preferred arrangement, sample 28 is positioned atop stage surface 26 without adhesive between the sample and the stage surface, followed by application of an adhesive to the interface of the sample and the stage surface about the perimeter of the sample. The adhesive then is allowed to adhere the sample to the stage surface.

According to one embodiment of the invention, the rate at which load is applied and released from the sample by the indenter is controlled so as to fall within certain preferred ranges, as it has been found in accordance with the invention that control of this parameter can affect the accuracy of measurement. In one embodiment, the invention involves loading a sample with an indenter at a rate of less than about 2 $\mu$ms per second, more preferably less than about 1 $\mu$m per second, more preferably less than about 0.5 $\mu$m per second, and most preferably less than about 0.1 $\mu$m per second. In another embodiment, the rate of unloading is less than about 1 $\mu$m per minute, more preferably less than about 0.5 $\mu$m per minute, more preferably less than about 0.2 $\mu$m per minute, and more preferably still less than about 0.1 $\mu$m per minute. A holding period of at least thirty seconds is recommended at the level of maximum applied load to ascertain time effect. Additionally, the rate of expansion or contraction of the contact area is smaller than the velocity of elastic waves in the material.

Another aspect of the invention involves particularly smooth application and/or release of load to a sample. The frame used to apply the load, according to this embodiment, applies and releases the load very smoothly (e.g., a stepped motor is not used; servohydraulic testing machines operated under displacement control typically cannot offer smooth enough motion for very accurate load/displacement analysis at unloading. It has been found that applying load with apparatus that applies and or releases load as smoothly as a screw-driven system, for example, an electromechanical screw system, is most advantageous. Smooth release of load contributes to accuracy of measurement of Young's modulus. Smooth application and/or release of load can be described in terms of load applied and/or released smoothly as a function of time. In particular, a mechanism that has a load versus time relationship that is essentially linear, rather than a stepped load versus time curve, is desired. Preferably, any "stepping" during loading and/or unloading will be less than about 0.1 Newton per second, more preferably less than about 0.05 Newton per second, and more preferably still less than about 0.01 Newton per second, depending on the material tested and maximum load softer materials require smoother release of load). An exemplary, non-limiting list of load-applying frames suitable for use with the invention include those made by INSTRON (4505, 5567, 5566, 8562), Canton, Mass.; MTS, Eden Praine, Minn.; and MTS 2/GL Electromechanic. A wide range of loads can be applied using the system of the invention. As discussed above, in preferred embodiments, the load applied is within a range between about 0.5N and 500 N, and a preferred frame can apply loads within this range.

One challenge in the use of sharp indenters is that in the measurement of polycrystalline materials, such as ceramics, where the size of each grain may be greater than the size of the tip of the indenter, it is possible that the mechanical properties of only one grain will be measured at one time at sufficiently low loads. In such a case, it can be advantageous to use a blunt indenter when bulk properties are measured. As used herein, the term "blunt" is given its usual meaning to include spherical indenters and the like and is given an additional, somewhat more precise definition as follows. Preferably, no portion of the blunt indenter surface that contacts the sample surface has a radius of curvature of less than about 15 $\mu$m, more preferably less than about 100 $\mu$m.

One feature of the invention is that a sample can be probed through a range of loads within microscale measurement through macro scale measurement whereby properties can be obtained. That is, with a single mechanical testing arrangement, a combination of properties previously assumed to be obtainable only with separate nanoscale and macro scale apparatus are determined. For very low loads, the classic theories of elastic and elasto-plastic deformation no longer suffice to interpret results accurately. Using the apparatus and methodology of the invention, uncertainties encountered in many existing micro-indentation techniques are circumvented since loads are low and at the same time high enough to probe average material properties.

Figure 7:
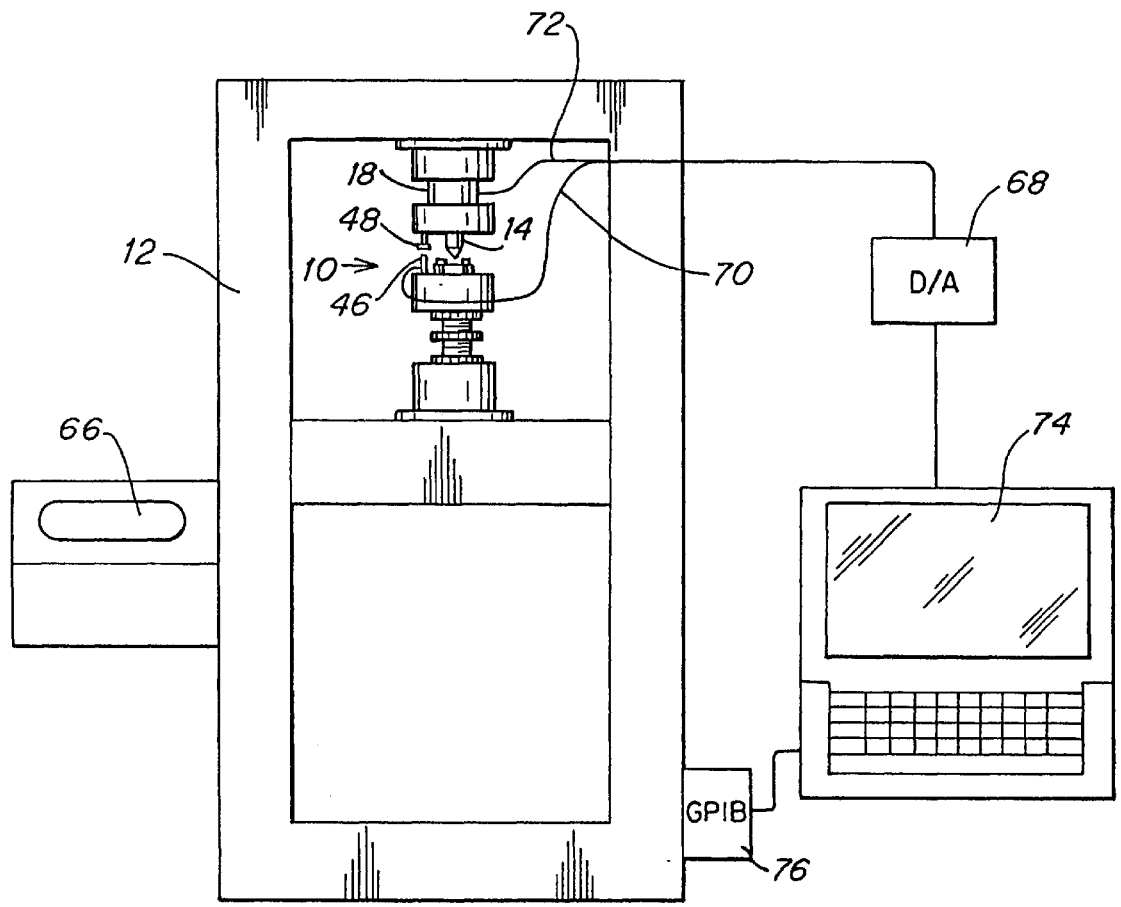
FIG. 7 illustrates schematically indentation measuring apparatus of the invention mounted in a load-applying frame and connected to automated measurement and data collection and analysis equipment.

In a preferred embodiment, indentation testing apparatus is adapted for mounting in any existing load-applying frame that meets the requirement for smooth application of load as described above. Referring to FIG. 2, indentation testing apparatus 10 is illustrated as mounted in a load-applying frame 12 such as an electromechanical testing system. This configuration is also shown in FIG. 7. Characteristics that make the apparatus adaptable for mounting in a variety of frames include mounting apparatus such as mounting flanges 44 and 22 as illustrated in FIG. 2. Apparatus 10 can be mounted on an existing frame, or removed from a frame and mounted on another frame, with routine mechanical operation using known fasteners such as bolts 50 (FIG. 2). It is not critical that disconnection from a frame and re-attachment to another frame be carried out by disconnecting and re-connecting flanges 22 and 44. Connection to an existing frame can be made via attachment of another portion of apparatus 10 that is designed to be connectable to the frame. As discussed above, threaded connection to the frame is preferred. This arrangement is distinguished from known, self-contained indentation testing apparatus that is defined by an integral arrangement including indenter and loading device as part of essentially a single unit that is not designed to be separated and, indeed, could not be separated without significant effort using more than conventional tools, and seriously compromising accuracy of measurement when re-assembled. Indentation apparatus from known, self-contained units including an integral loading device cannot be removed from such units without other-than-routine procedures such as cutting or extensive disassembly, and typically are not equipped with components that would render them readily mountable on an existing frame. Testing apparatus 10 can be installed in an existing frame rapidly (on the order of several hours to a day by one person of ordinary skill in the art).

When apparatus 10 is installed on a new frame and secured thereto, minimal recalibration of the displacement sensor, routine examination of the accuracy of the load cell, etc. is all that is needed. As discussed above, when apparatus 10 is rigidly secured to the frame, preferably via threaded fasteners, adjustable and other movable portions of the apparatus can be very securely immobilized, preferably also via threaded fasteners, so that the overall arrangement is very stiff.

Since known, self-contained indentation testing units typically include load-applying equipment constructed in conjunction with the indentation tester as an integral unit, the apparatus of the present invention typically can be made much more inexpensively than prior art indentation testing apparatus. In addition, loading apparatus of prior art arrangements is essentially useless for purposes other than applying load in indentation testing. Thus, apparatus of the present invention does not necessarily dominate a load-applying frame and prevent its use in other common mechanical tests such as tensile, compressive, and bending. The apparatus of the invention can be readily removed from a frame, the frame can be put to another use, and the apparatus returned to the frame. This makes it a routine instrument of less delicate character than, for example, the Nanoindenter™, capable of reproducibility and standardization, and very economical with respect to amount of material, cost, and time spent to obtain mechanical parameters.

By following the teachings described herein, a particularly preferred embodiment of indentation testing apparatus can be readily constructed that is readily mountable in and removable from a load-applying frame using common fasteners, that is capable of determining, from a load/depth relationship, one of Young's modulus, yield strength, tensile strength, strain hardening exponent, and hardness, with less than about 20% error. In a more preferred embodiment, such measurements can be routinely made with less than about 10% error, and in a most preferred embodiment with less than about 5% error. Error is determined by comparison to conventional macro scale tests.

Methodology

The invention also provides new methodology for indentation analysis that involves direct derivatization of contact area from load/displacement analysis.

The following description of this aspect of the invention is divided into methodology associated with sharp indenters and methodology associated with blunt indenters.

Sharp Indenters

The following methodology is based on dimensional analysis coupled with extensive finite element computations that take into account the three-dimensional aspects of pyramidal indentations. Some of the equations below are known. For sharp indenters, the ratio of residual depth ($h_r$) to maximum depth ($h_{max}$) defines the strain hardening exponent (n). From the strain hardening exponent, the contact area at loading can be deduced from methodology described below. From the initial slope (dP/dh) of the unloading portion of the load/depth data and the contact area at unloading, the elastic modulus can be deduced as shown below. A correction for diamond tip compliance can be taken into account. The yield strength can be deduced from the loading part of the load/depth data.

Figure 5:
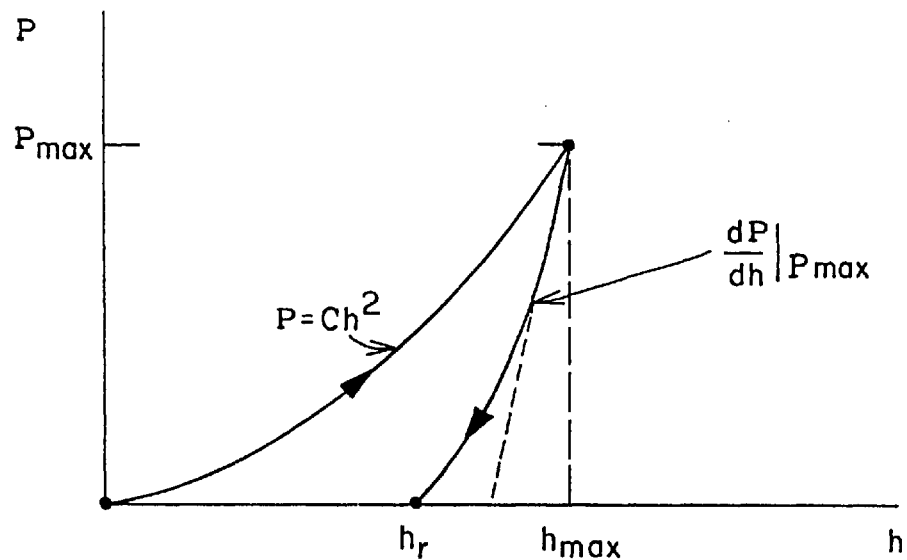
FIG. 5 is illustrative of a typical load/depth curve of a pyramidal indentation test.

According to FIG. 5 (representative of a typical load/displacement curve using a pyramidal indenter) the following values are determined experimentally during a single load/unload measurement: $h_r/h_{max}$, dP/dh at $P_{max}$, and $P/h^2$. Using $h_r/h_{max}$, the parameter H/E is obtained according to equation 1.

$$\frac{H}{E} = \frac{\sigma_u - \sigma_y}{0.3E} = 1 - 0.1419\frac{h_r}{h_{max}} - 0.9568\left(\frac{h_r}{h_{max}}\right)^2 \qquad \text{Eq. 1}$$

With the parameter H/E from equation 1, the maximum normalized contact area $A_{max}/h_{max}^2$ is given according to equation 2.

$$\frac{A_{max}}{h_{max}^2} = 9.96 - 12.64\frac{H}{E} + 105.42\left(\frac{H}{E}\right)^2 - 229.57\left(\frac{H}{E}\right)^3 + 157.67\left(\frac{H}{E}\right)^4 \qquad \text{Eq. 2}$$

Using dP/dh at $h_{max}$ the combined elastic modulus E* can be obtained according to equation 3.

$$\frac{E^*}{1-v^2} = \frac{1}{C^*}\frac{1}{\sqrt{A_{max}}}\left.\frac{dP}{dh}\right|_{h_{max}} \qquad \text{Eq. 3}$$

where C* is 1.142 for the Vickers indenter geometry and 1.167 for Berkovich, and (v) is the Poisson ratio (v is approximately 0.3 for most materials, and can be obtained with accuracy from the literature; specifically, v=0.33 for metals, 0.25 for ceramics, $1/(2\sqrt{2})$ for optimum error; default value). To correct for the diamond tip compliance, equation 4 is used.

$$\frac{E}{1-v^2} = \frac{1}{\frac{1-v^2}{E^*} - \frac{0.96}{900\,GPa}} \qquad \text{Eq. 4}$$

where the elastic modulus of the diamond is taken as 900 GPa and its Poisson ratio as 0.2 (E and E* in GPa).

It can be appreciated that accurate determination of contact area at loading is of paramount importance according to this methodology.

To compute yield strength the following ratio is examined: $P_{max}/(A_{max} E \tan \beta)$ where $\beta=22°$ for Vickers and 24.7° for Berkovich. If this ratio is less than 0.1, then yield strength is given by equation 5.

$$\sigma_y \approx \sigma_u \approx \frac{P_{max}}{2.8 A_{max}} \quad \text{Eq. 5}$$

If the ratio above for computing yield strength is greater than or equal to 0.1, then the constant $C=P/h^2$ (Kick's law) is taken as follows: For elasto-plastic behavior, equations 6 and 7 are used, together with the value of the parameter H/E, defined in equation 1, above.

$$C = 1.220(\tan 22°)^{-2} \sigma_y \left(1 + \frac{\sigma_u}{\sigma_y}\right)\left(1 + \ln\frac{E\tan 22°}{3\sigma_y}\right) \quad \text{Eq. 6}$$

(for Vickers)

$$C = 1.273(\tan 24.7°)^{-2} \sigma_y \left(1 + \frac{\sigma_u}{\sigma_y}\right)\left(1 + \ln\frac{E\tan 22°}{3\sigma_y}\right) \quad \text{Eq. 7}$$

(for Berkovich)

Mayer's hardness ($P_{av}$) is defined according to equation 8.

$$P_{av} = \frac{P_{max}}{A_{max}} \quad \text{Eq. 8}$$

To obtain the strain hardening exponent (n), equation 9 is used.

$$n = \frac{\ln \sigma_u - \ln \sigma_y}{\ln 150} \quad \text{Eq. 9}$$

That is, according to equations 1–9 above, by measuring load versus displacement of essentially any type of material at load as low as about 0.5 N or up to about 500 N, the area of contact between the indenter and the sample surface, at loading, is calculated directly. Then, elastic modulus is calculated, then yield strength and ultimate tensile strength, and finally strain hardening exponent is derived.

Spherical Indenter

The following methodology results in derivation of contact area directly from load/depth measurement, and subsequent calculation of mechanical properties. The process is based on the examination of the loading portion of the load/depth measurement, the initial portion of which is associated with the elastic modulus and the later portion of which is associated with the fully plastic region. In certain cases the unloading portion of the load/depth measurement may be useful as well.

Figure 6:
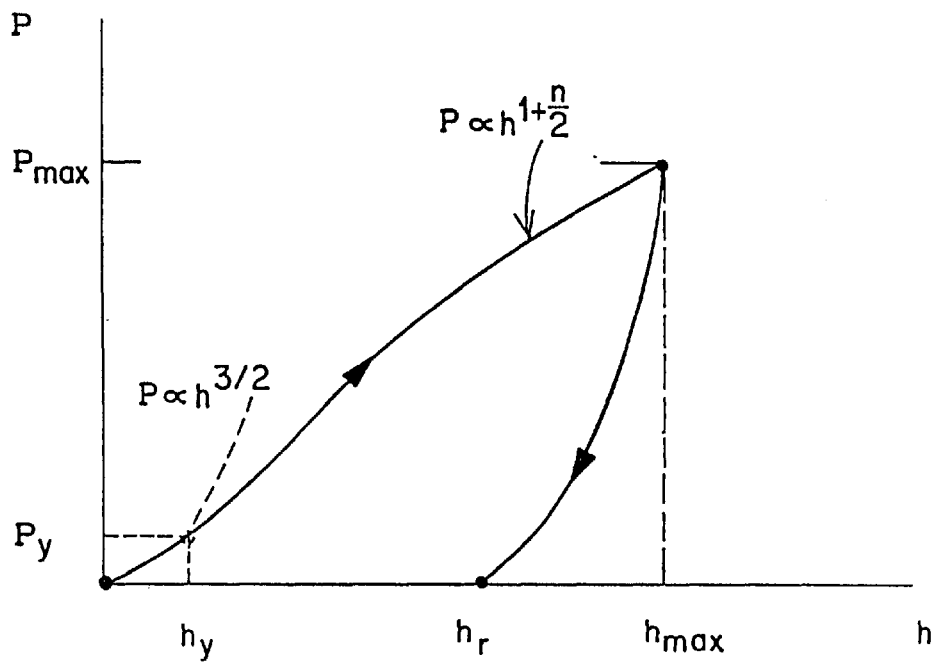
FIG. 6 is illustrative of a typical load/depth curve of a spherical indentation test.

The elastic modulus is computed by fitting the initial portion of the load/depth curve of FIG. 6 according to equation 10.

$$\frac{E^*}{1-v^2} = \left(\frac{9}{8}D\right)^{-1/2} P h^{-3/2} \quad \text{Eq. 10}$$

where D is the diameter of the spherical indenter. From P and h values within the region of validity of the elastic solution on the curve (the region of the curve according to P is proportional to $h^{3/2}$), $E^*$ can be determined.

To correct for the compliance of the indenter, equation 11 is used where E' is the indenter's elastic modulus and v' is the Poisson ratio.

$$\frac{E}{1-v^2} = \frac{1}{\frac{1-v^2}{E^*} - \frac{1-v'^2}{E'}} \quad \text{Eq. 11}$$

To obtain the strain hardening exponent (n) the mainly plastic portion of the load/depth relation is obtained via equation 12, which is an expression derived from Mayer's law in terms of load/depth relationship.

$$P \propto h^{1+\frac{n}{2}} \quad \text{Eq. 12}$$

n is determined by measuring the slope of log P—log h, which gives the value of 1+n/2.

Contact area at maximum load ($A_{max}$) is derived from equation 13:

$$A_{max} = \pi D h_{max} c^2 = \pi a_{max}^2 \quad \text{Eq. 13}$$

here $a_{max}$ is the contact radius at maximum load and where c is related to strain hardening (n) by equation 14.

$$\frac{1}{c^2} \approx 2\left(\frac{(2/n)}{(2/n)+1}\right)^{2((1/n)-1)} \quad \text{Eq. 14}$$

Where the strain hardening exponent (n) is greater that 1/3.4, sinking-in at the perimeter of the indentation contact occurs. At n less than 1/3.4, pile-up occurs. Failure to take into account sinking-in and pile-up compromises accuracy in measurement of the true area of contact of the indenter under load.

Validity of the above methodology can be confirmed by ensuring that measurements are taking place where the region of contact between the indenter and the sample is no more than 20% of the diameter of the indenter.

Next, the average pressure ($P_{av}$ force divided by true contact area) is calculated according to equation 8 taking $A_{max}$ from equation 13.

To compute the yield strength, first the characteristic strain at maximum load is computed in accordance with equation 15.

$$\epsilon_{max} = \frac{16}{9\pi}\left(\frac{2/n}{2/n+1}\right)^{1/n} \frac{a_{max}}{D} \quad \text{Eq. 15}$$

Yield strength is given by equation 16.

$$\sigma_y = \frac{P_{max}}{3A_{max}}\left(\frac{0.002}{\epsilon_{max}}\right)^n \quad \text{Eq. 16}$$

The end of the elastic regime occurs at a point ($h_y$, $P_y$) of the load/depth curve (FIG. 6) given by $$P_y = \frac{9}{16}\left(\frac{D(1-v^2)}{2E^*}\right)^2 (3\pi\sigma_y)^3 \quad \text{Eq. 17}$$

$$h_y = \left(\frac{9}{16}\right)^{1/3} \left(\frac{P_y(1-v^2)}{E^*}\right)^{2/3} \left(\frac{2}{D}\right)^{1/3} \quad \text{Eq. 18}$$

It may be so that the level at the yield initiation is too low and makes it difficult for the elastic modulus to be captured directly at loading (Eq. 10). Alternatively, the residual depth $h_r$, (See FIG. 6) may be used as follows $$\frac{E^*}{1-v^2} = \left(P_{av}\frac{9\pi}{16}P_{max}\right)^{1/2} \Big/ (h_{max} - h_r)^2 \qquad \text{Eq. 19}$$

Automated Set-Up for Experimentation and Analysis

Illustrated in FIG. 7 is equipment that allows automated testing of a sample and automated analysis of data obtained from testing. A control panel 66 can be used to manually control the loading frame 12, and load applied. A fast D/A converter 68 is connected via lead 70 to displacement sensor 46 and via lead 72 to load cell 18 so as to acquire load and indentation depth measurements via a computer 74. LAB-VIEW software can be used for data acquisition. Testing parameters, such as maximum load and indenter type, are fed into the computer 74 which then directly acquires the data via the D/A converter and controls the test by standard general purpose interface bus (GPIB) connections 76. The computer 74 also can be arranged to control an X-Y stage (not shown) upon which the specimen can be mounted, and other adjustable components such as mirror 48 so that an entire set-up and testing procedure is essentially automated, and indentations can be performed at pre-selected locations serially.

Figure 8:
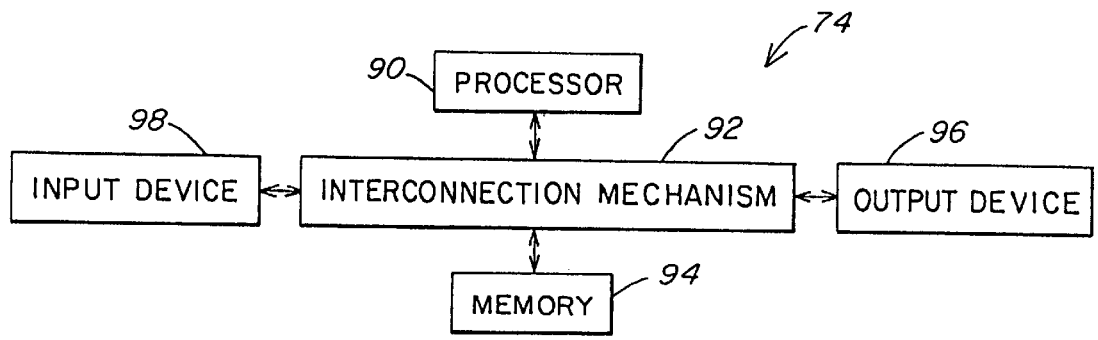
FIG. 8 is a block diagram of an example computer system which may be used to automate the practice of the present invention.

An example computer system 74 is in FIG. 8. The computer 74 generally includes a processor 90 connected to a memory 94 via an interconnection mechanism 92. An input device 98 is also connected to the processor and memory system via the interconnection mechanism, as is an output device 96.

It should be understood that one or more output devices 96 may be connected to the computer 74. Example output devices include cathode ray tube (CRT) displays, liquid crystal displays (LCD), printers, additional storage devices and control outputs via the GPIB connections 76, and communication devices such as a modem. It should also be understood that one or more input devices 98 may be connected to the computer 74. Example input devices include GPIB connections 76, a keyboard, keypad, track ball, mouse, pen and tablet and communication device. It should be understood the invention is not limited to the particular input or output devices used in combination with the computer 74 or to those described herein.

The computer 74 may be a general purpose computer system which is programmable using a high-level computer programming language, such as "C," "Pascal" or "Visual Basic." The computer may also be specially programmed, using special purpose hardware. Additionally, the computer 74 may be a multiprocessor computer system or may include multiple computers connected over a computer network.

In a general purpose computer system, the processor 90 is typically a commercially available processor, of which the series x86 processors, available from Intel, and the 680X0 series microprocessors available from Motorola are examples. Many other processors are available. Such a microprocessor executes a program called an operating system, of which UNIX, DOS and VMS are examples, which controls the execution of other computer programs and provides scheduling, debugging, input/output control such as for the GPIB connections, accounting, compilation, storage assignment, data and memory management, communication control and related services. The processor and operating system define a computer platform for which application programs in various programming languages may be written. It should be understood the invention is not limited to a particular computer platform, particular processor, or particular high-level programming language.

Figure 9:
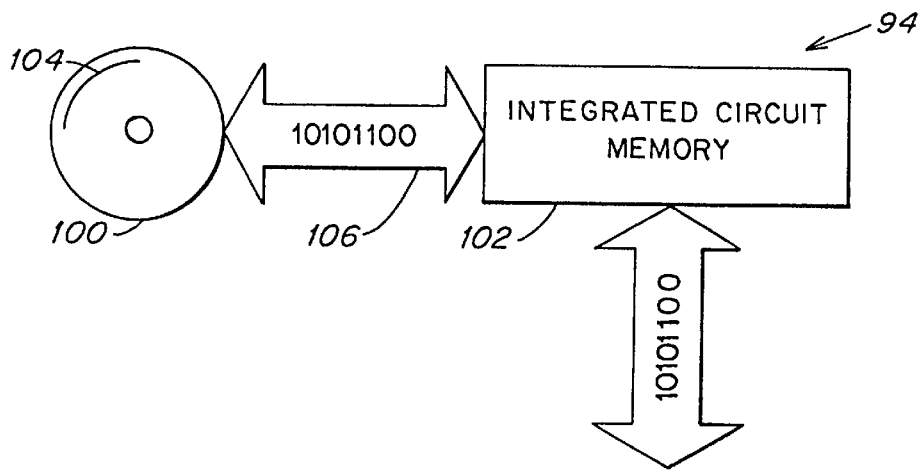
FIG. 9 is a block diagram of a memory system shown in FIG. 8.

An example memory system 94 will now be described in more detail in connection with FIG. 9. A memory system typically includes a computer readable and writeable nonvolatile recording medium 100, of which a magnetic disk and tape are examples. The disk may be removable, known as a floppy disk, or permanent, known as a hard drive. Where the medium 100, a disk, which is shown in FIG. 9, has a number of tracks, as indicated at 104, in which signals are stored, typically in binary form, i.e., a form interpreted as a sequence of one and zeros such as shown at 106. Such signals may define an application program to be executed by the microprocessor, or information stored on the disk to be processed by the application program. Typically, in operation, the processor 90 causes data to be read from the nonvolatile recording medium 100 into an integrated circuit memory element 102, which is typically a volatile, random access memory such as a dynamic random access memory (DRAM) or static memory (SRAM). The integrated circuit memory element 102 allows for faster access to the information by the processor than does the medium 100. The processor generally manipulates the data within the integrated circuit memory 102 and then copies the data to the medium 100 when processing is completed. A variety of mechanisms are known for managing data movement between the medium 100 and the integrated circuit memory element 102, and the invention is not limited thereto. It should also be understood that the invention is not limited to a particular memory system 94.

Figure 10:
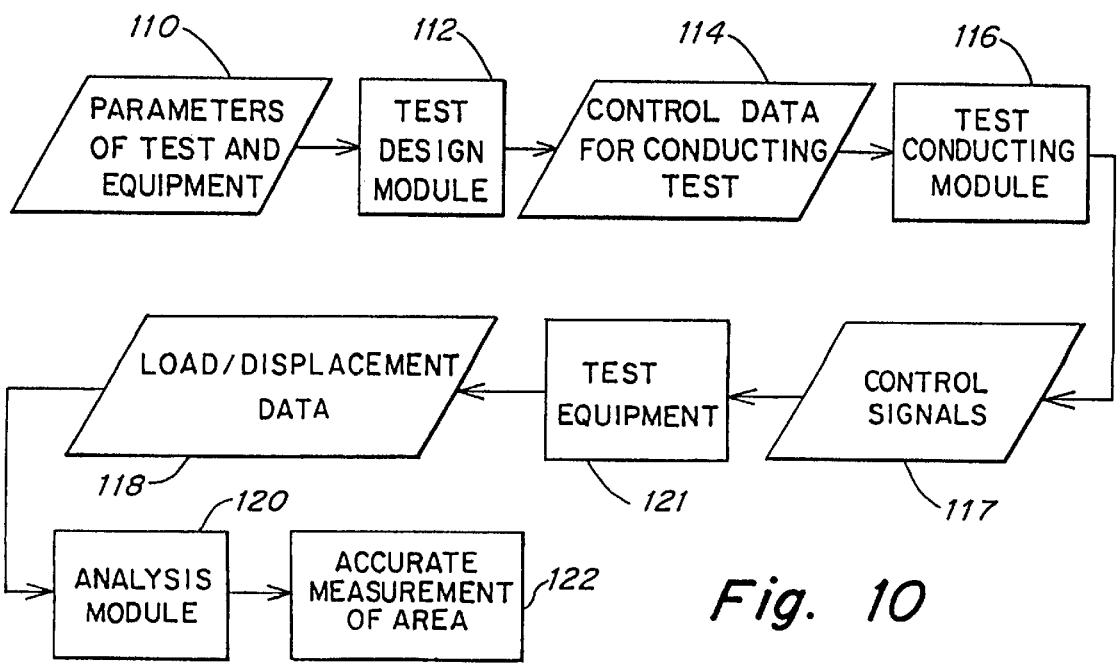
FIG. 10 is a data flow diagram representative of methodology for designing and conducting and analyzing results in accordance with the invention.

A system for automated testing is shown in FIG. 10. This system includes three interconnected modules, each of which may be implemented using a computer program to run on a computer 74, each of which is an aspect of the invention. First module is a test design module 112 which receives, as an input, parameters of a test and the equipment to be used in the test as indicated 110. Test design module then outputs control data 114 which is then used in conducting a test. The control data 114 is received by a test conducting module 116 which outputs control signals to the test equipment 117 to control its movement and to control the sensors and which in turn outputs the load/displacement data as indicated at 118. The load/displacement data 118 is applied to an analysis module 120 which outputs an accurate measurement of the area of contact of the probe with the material, as indicated at 122. This measurement may be used to determine the mechanical properties of the material being tested.

Figure 11:
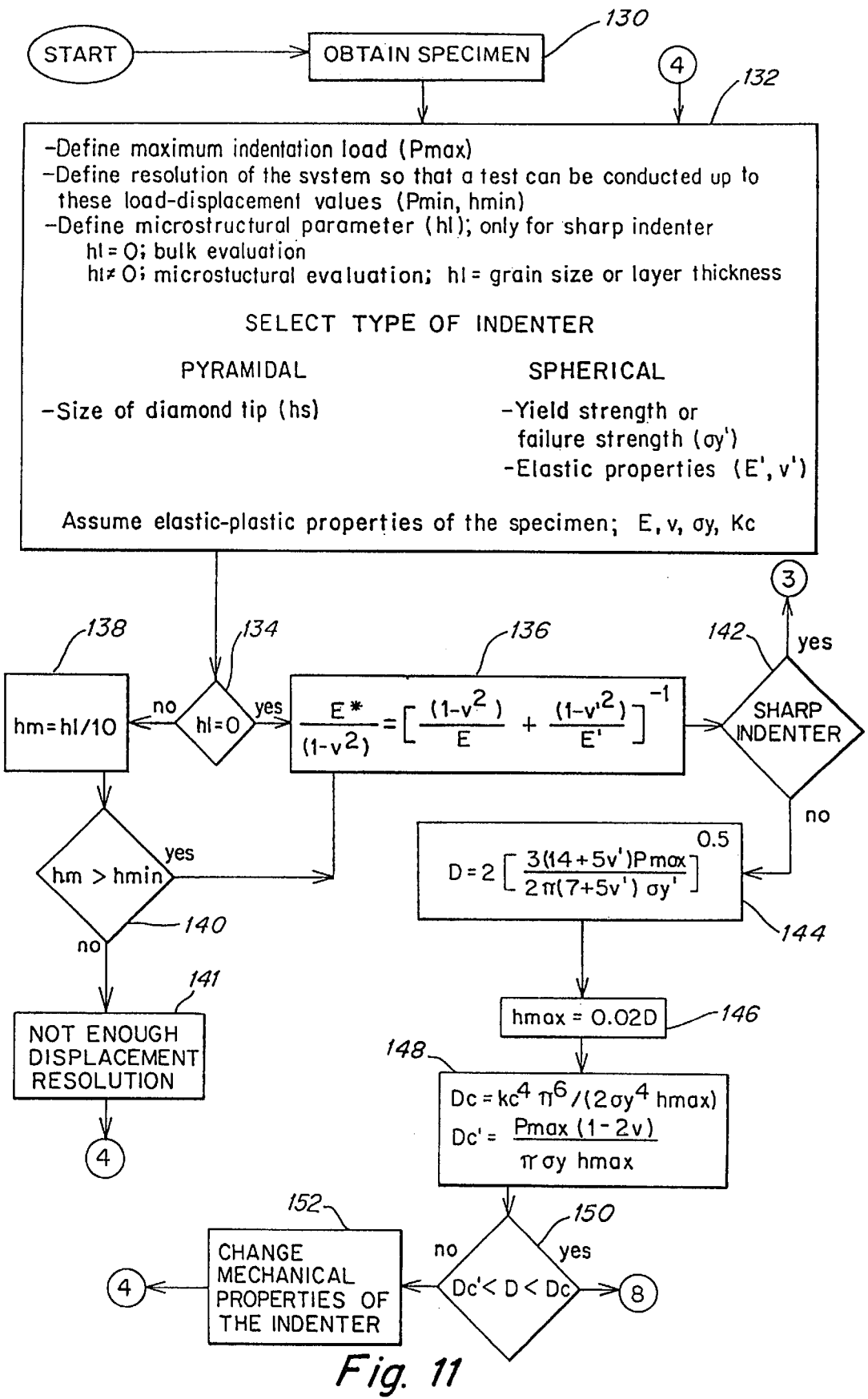
FIG. 11 is a flow chart describing how control data for conducting a test is determined from parameters of the test and equipment.
Figure 12:
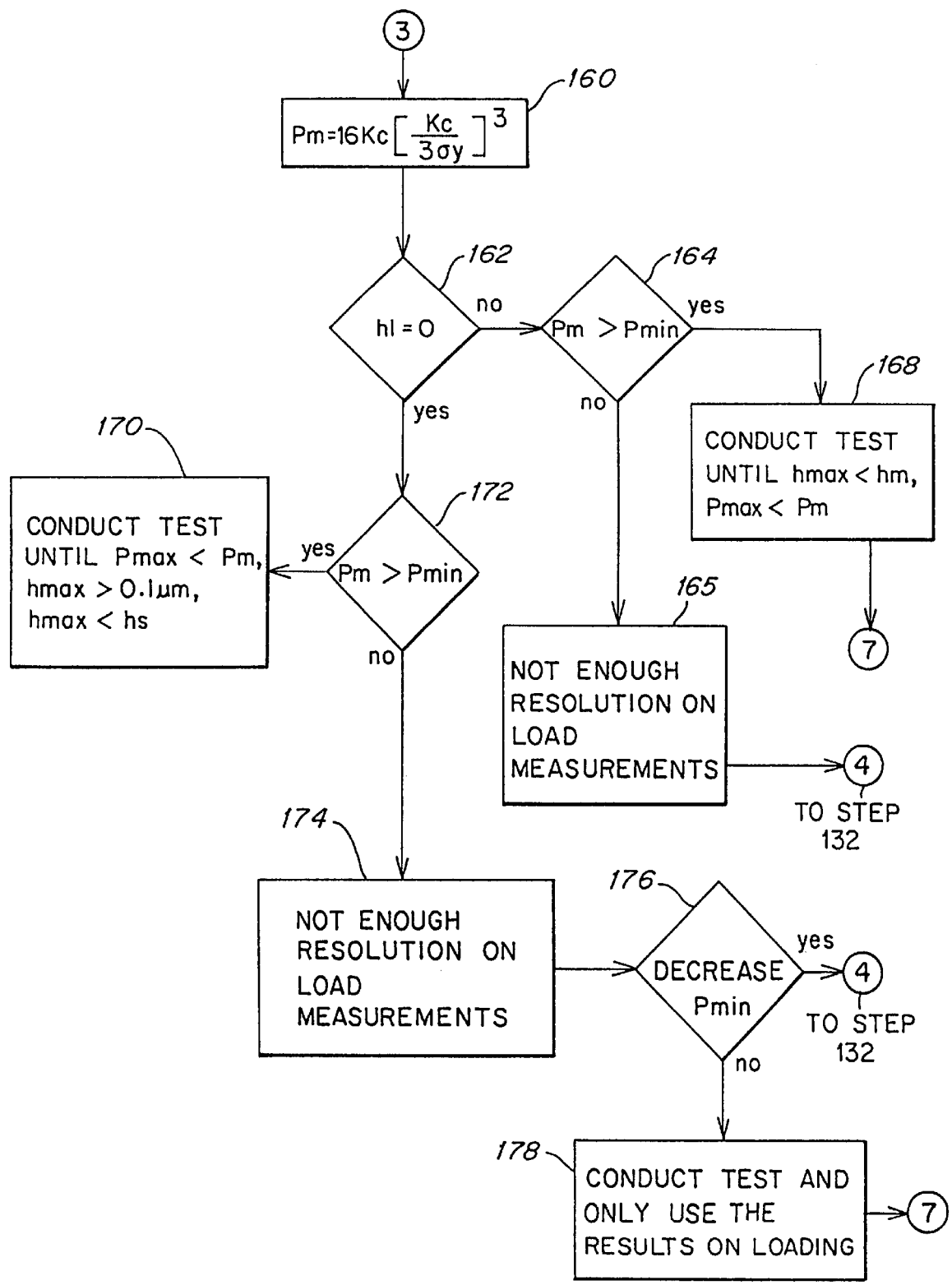
FIG. 12 is a flow chart describing how additional control data is determined and how a test is conducted for a sharp indenter.
Figure 13:
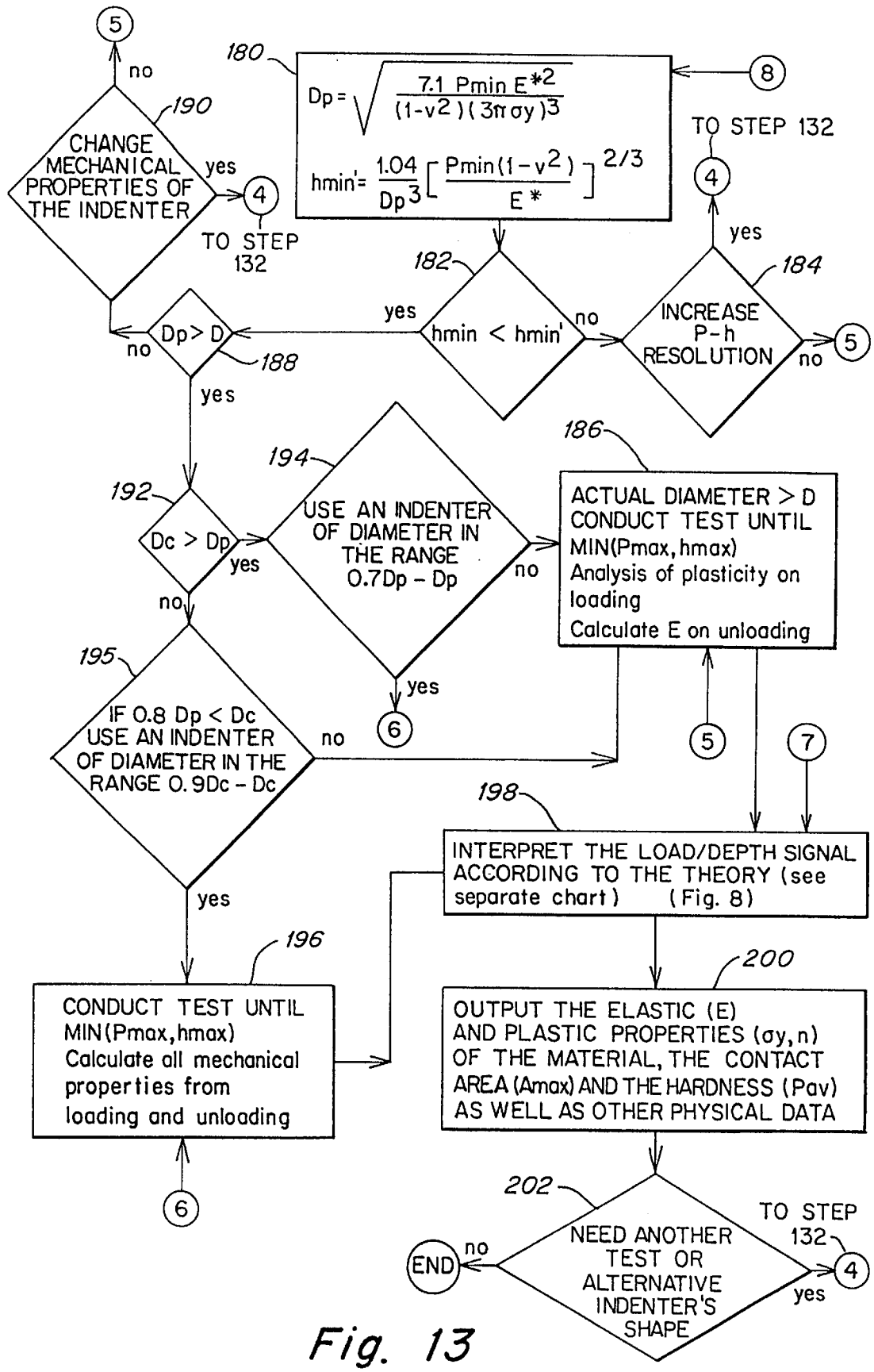
FIG. 13 is a flow chart describing how additional control data is determined and a test is conducted for spherical indenters.

Each of the modules 112, 116 and 120 will now be described in more detail in connection with FIGS. 11 through 15. The process of designing a test will be described first. In connection with FIGS. 11–13. FIGS. 11–13 describe a preferred, optimized arrangement for selecting optimal test parameters such as sphere diameter, maximum load, material of the indenter, and the like. The particular order and arrangement of the steps involved could be altered by one of ordinary skill in the art to arrive at an equivalent result. The inventive nature of the process illustrated in FIGS. 11–13 involves using the criteria and equations set forth to arrive at the result, by whatever means.

The first step of defining a test is obtaining a specimen (step 130). Parameters of the test are then defined by an individual in step 132. Parameters to be defined include the maximum indentation load ($P_{max}$), the resolution of the system ($P_{min}$, $h_{min}$). If a sharp indenter will be used, a microstructural parameter ($h_f$) is defined. This parameter can be defined to be zero to indicate bulk evaluation. Microstructural evaluation can be indicated by a non-zero value for this parameter. This value may indicate grain size or layer thickness, for example. The type of indenter is also input. For example, the indenter may be sharp, such as a pyramidal indenter, or may be blunt. The size of the diamond tip ($h_s$) of a sharp indenter is input by the individual. For a blunt indenter, the yield strength or failure strength ($\sigma_y'$) and elastic properties (E', the Young's modulus of the blunt indenter and the Poisson ratio (v') of the blunt indenter) are also input. Elastic and plastic properties of the specimen are then assumed, including the Young's modulus (E'), Poisson ratio (v'), the yield strength ($\sigma_y'$) and fracture toughness $K_c$.

Having defined the parameters of the indenter and the system, if bulk evaluation is to be performed (as determined by step 134), the combined elastic modulus of the indenter and sample is determined according to the assumed properties in step 136. If bulk evaluation is not to be performed, but rather microstructural evaluation is to be performed, the grain size or layer thickness is compared to the resolution of the system which needs to be larger than a tenth of the microstructural feature under consideration (i.e., as shown in steps 138 and 140) of FIG. 11. If the system does not have enough displacement resolution (step 141) to perform the microstructural evaluation, the test must be redesigned in step 132. If there is enough displacement resolution in the system, processing continues with step 136 described above.

Having computed the assumed combined effective elastic modulus of the indenter and sample based on the assumed properties of the specimen and the input properties of the indenter, the control data for the test is then determined, according to the indenter type as indicated in step 142. The process for sharp indenters will be described below in connection with FIG. 12. Some initial steps for blunt, for example spherical indenters will continue to be described in connection with FIG. 11.

For a blunt indenter, the minimum diameter of the indenter to be used in the test is then determined as a function of the maximum indentation level ($P_{max}$), the yield or failure strength in uniaxial compression of the indenter, and the Poisson ratio of the indenter (step 144). The measured maximum indentation depth, (penetration or displacement) then is determined as a function of this determined diameter in step 146. Additional parameters are determined in step 148. The diameter of the indenter below which "ring" cracking can develop in the sample (Dc') and the diameter above which "radial" cracking could develop (Dc) are defined in step 148 in relation with the input of the test. If the determined diameter is not between these two additional parameters, as determined in step 150, the mechanical properties of the indenter need to be changed as indicated at 152, which causes a request for a redefinition of the test in step 132. If the determined diameter D is acceptable, processing continues as described in more detail below in connection with FIG. 13.

Referring now to FIG. 12, the determination of test parameters for conducting tests with sharp indenters will now be described. A value $P_m$ which evaluates the resistance against cracking in the sample is first calculated in step 160. If the test to be performed involves microevaluation of the sample, as determined in step 162, it is then determined whether there is enough resolution in the system for the load measurements. If the value $P_m$ is not greater than the minimum load that can be applied to the sample, as determined in step 164, there is not enough resolution for the load measurements (step 165) and the test should be redefined in step 132. If there is enough load resolution, the test is then performed in step 168 until the maximum measured indentation depth and the maximum load applied to the sample with the indenter are less than the determined values $h_m$ and $P_m$.

For a bulk test with a sharp indenter (as determined in step 162), if the value $P_m$ is greater than the load resolution of the system, the test is then performed until the maximum load applied to the sample is less than the value $P_m$, the maximum indentation depth is greater than the radius of the indenter tip, typically one tenth of a micron and is less than $h_s$ as indicated at step 170. If $P_m$ is not greater than $P_{min}$, as determined in step 172, there is not enough resolution for the load measurements, as indicated at 174, and $P_{min}$ should be decreased (step 176). If the minimum load cannot be decreased, as may be determined in response to user input, the test is conducted using only the results on loading as indicated at 178. Otherwise, the test may be redefined by returning to step 132.

After conducting the test in either step 168, 170 or 178, processing continues with the analyzing of the results, which will be described in more detail below in connection with FIGS. 13–15.

Determination of control parameters for a test with a spherical indenter will now be described in connection with FIG. 13. This process continues from step 150 in FIG. 11 with step 180 in FIG. 13 for determining the values $D_p$ and $h_{min}'$ which define a load-displacement range where the test will capture the elastic response of the material. If $h_{min}'$ is not greater than $h_{min}$ as determined in step 182, and if it is possible to increase the load-depth resolution of the system, as determined in step 184 (possibly in response to user input) the test is redefined in step 132 of FIG. 11. Otherwise, the test is actually conducted in step 186, which will be described in more detail below. If $h_{min}$ is less than $h_{min}'$, as determined in step 182, the value $D_p$ is compared to the calculated diameter. If $D_p$ is not greater than the calculated diameter, as determined in step 188, and if the mechanical properties of the indenter can be changed, as determined in step 190 (possibly in response to user input), the test is redefined by returning to step 132, otherwise the test is conducted in accordance with step 186 to be described in more detail below. If the value $D_c$ is greater than the value $D_p$ and if it is possible to use an indenter of diameter in the range of 70% to 100% of the value $D_p$, as determined in step 194, the test is conducted in accordance with step 196 to be described in more detail below. Otherwise the test is conducted in accordance with step 186, also to be described in more detail below.

For $D_p$ smaller than $D_c$ and if 80% of the $D_p$ value is less than the $D_c$ value and if an indenter is available having a diameter in the range of 90% to 100% of the DC value (step 195), the test is conducted in accordance with step 196. Otherwise, the test is conducted in accordance with step 186.

Given the parameters defined in the steps of FIGS. 11 through 13, the test on the sample is conducted in any of steps 168, 170, 178, 186 and 196. In step 186, a test is conducted until the minimum of $P_{max}$ and $h_{max}$ is obtained. Plasticity is analyzed upon loading and the Young's modulus is calculated upon unloading. In step 196, the test is conducted until the minimum of $P_{max}$ and $h_{max}$ are obtained. All mechanical properties are calculated upon loading and unloading.

Each of these steps may be implemented using the test conducting module 116 of FIG. 10. The test conducting module may be a general purpose test module which needs to be programmed to perform the test defined by the given and calculated parameters, or a custom program may be defined which receives the given and calculated parameters as input and which performs the step that a generic testing may perform. For example, generic control software may be programmed with a control program which prompts a user for parameters of a test determined by the test design module 112. Suitable to systems for this control include FLAPS™ software of INSTRON, Series X or equivalent.

As described above in connection with FIG. 7, a displacement sensor 46 and a load cell 18 are connected through the computer, for example, via a digital to analog converter 68. The load and depth signals are interpreted to obtain the elastic and plastic properties of the sample in step 198. These determined properties may be output to a display and/or stored in the memory of the computer in step 200. If another test is needed or an alternative indenter shape is to be used, (step 202) the new test can be designed by returning to step 132 (FIG. 11).

The interpretation of the load/depth signal for tests performed using a sharp indenter will now be described in connection with FIG. 14. The first step 210 involves computing the tangent elasto plastic modulus in accordance with equation 1. Next, the maximum contact area is computed in step 212 according to equation 2. The combined Young's modulus is then computed in step 214 according to equation 3. Corrections for diamond tip compliance are then made in accordance with equation 4 in step 216. Hardness is then computed using equation 8 in step 218. The characteristic strain is then computed (step 220) using the following equation:

$$\frac{P_{max}}{A_{max} E \tan \beta} \quad \text{Eq. 20}$$

If the characteristic strain is less than 0.1, yield and characteristic strength values are computed in step 222 according to equation 5. Otherwise, if the computed characteristic strain is greater than or equal to 0.1, yield and characteristic strength values are computed in step 224 according to equation 1 and equation 6 or 7. After computing the yield and the characteristic strength in steps 222 or 224, strain hardening is then computed according to equation 9 in step 226.

Figure 15:
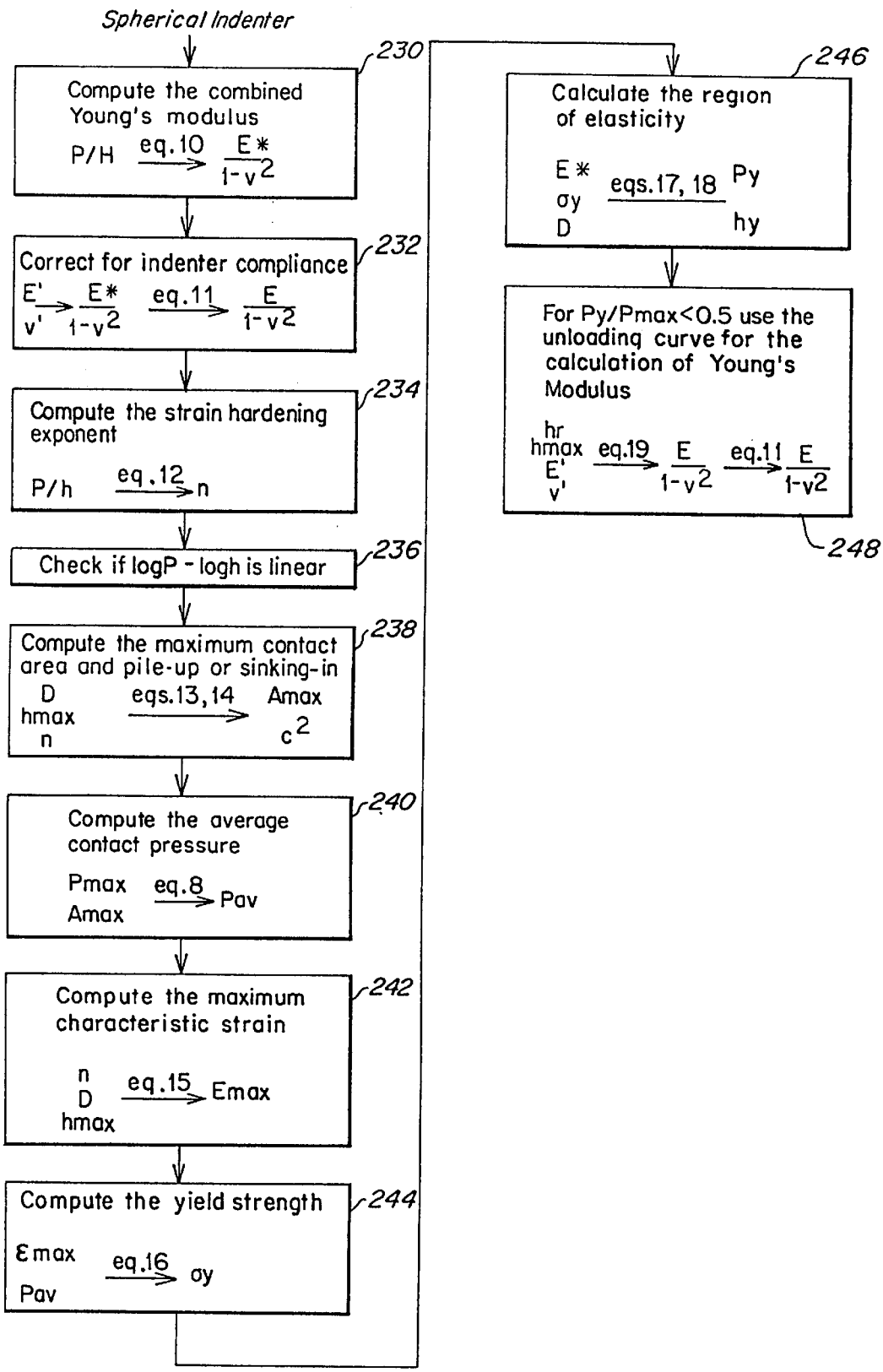
FIG. 15 is a flow chart describing how a load/displacement data is analyzed to obtain a mechanical property information for a spherical indenter.

For a blunt indenter, such as a spherical indenter, the load/depth signal is analyzed in accordance with FIG. 15. First, the combined Young's modulus is computed in step 230 according equation 10. Corrections for indenter compliance are then made in step 232 according to equation 11. The strain hardening exponent is then computed in accordance with equation 12 in step 234. The log-log curve of the load/depth relationship is then analyzed to determine whether it is linear in step 236, hence whether the test is conducted in the fully plastic regime and validates the theoretical plastic model assumed. The maximum contact area, pile-up or sinking-in effects are then computed in accordance with equations 13 and 14 in step 238. The average contact pressure is computed in step 240 according to equation 8. The maximum characteristic strain is then computed in accordance with equation 15 in step 242. Next, in step 244, the yield strength is computed according to equation 16. The region of elasticity is determined in step 246 using equations 17 and 18. Finally, for the case where the ratio of $P_y$ to $P_{max}$ is smaller than 0.5, the unloading curve for the calculation for Young's modulus is used in step 248, using equations 19 and 11.

Figure 14:
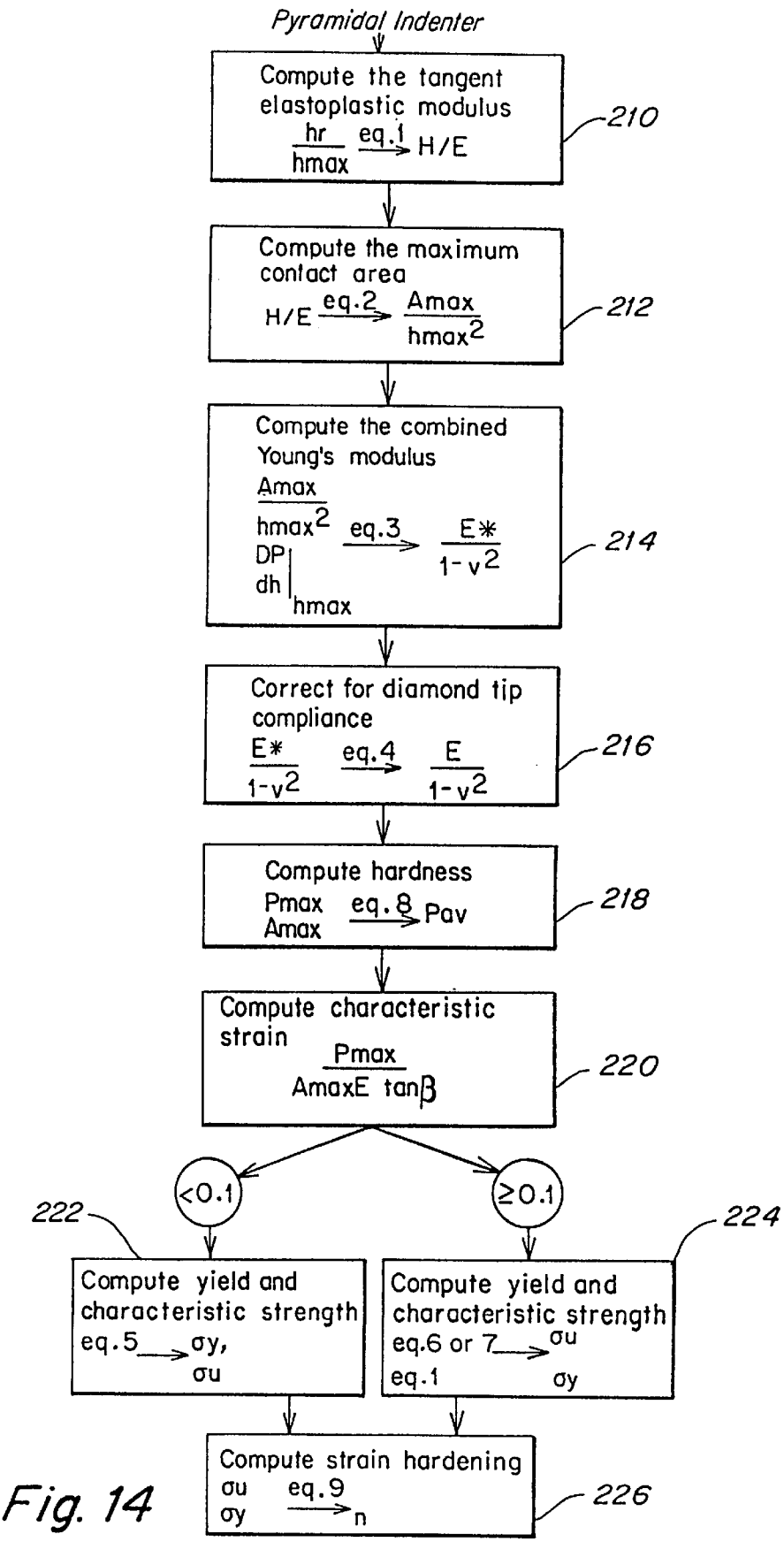
FIG. 14 is a flow chart describing how a load/displacement data is analyzed to obtain a mechanical property information for a sharp indenter.

The calculations performed in FIGS. 14 and 15 may be implemented as part of the analysis module 120 of FIG. 10. It should be understood that the load/displacement data will be stored in the memory system 94 of the computer 74 prior to analysis. Thus, since this data can be stored indefinitely, the analysis module may be used to analyze previously obtained results from other tests. Additionally, the test module, test execution module and analysis modules may be located in different computer systems and different locations.

The above methodology can be programmed into a computer such as shown in FIGS. 7–9 by one of ordinary skill in the art so that with a single command or series of commands, one, several, or all of the determinations described above can be carried out. Known mechanical properties of materials can be installed on the computer in the form of a data base so that the apparatus can help the user in the definitions proposed in step 132 of FIG. 11.

EXAMPLES

The function and advantages of these and other embodiments of the present invention will be more fully understood from the examples below. The following examples are intended to illustrate the benefits of the present invention, but do not exemplify the full scope of the invention.

Example 1
Determination of Young's Modulus (E) in a Ceramic Material.

Figure 16:
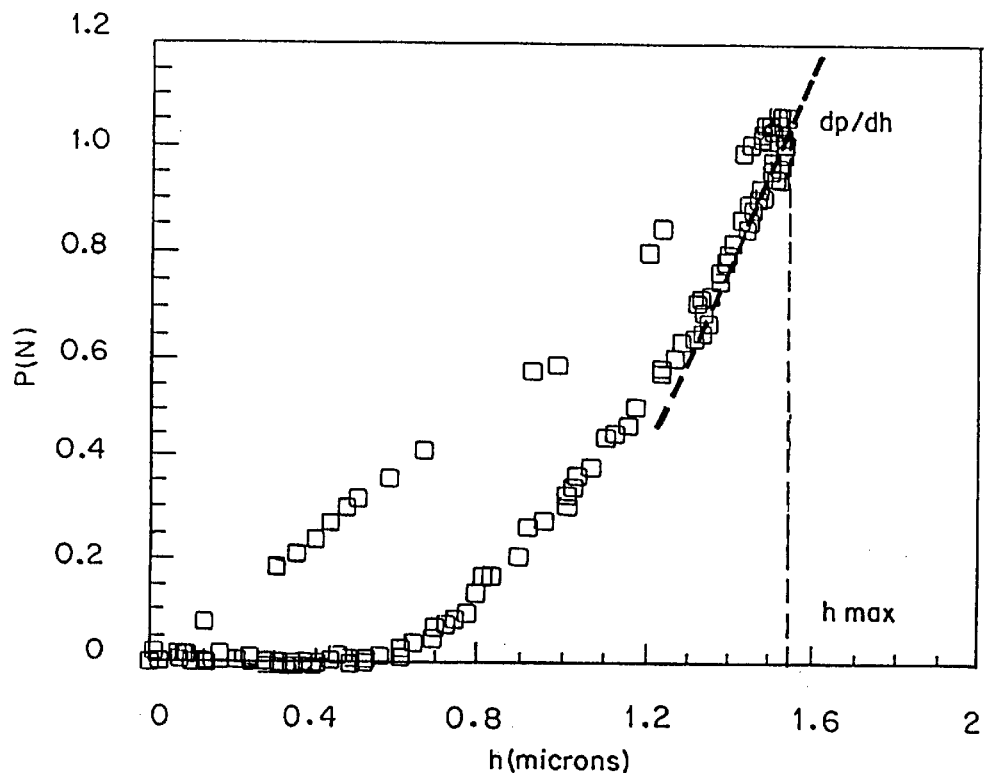
FIG. 16 illustrates experimentally-measured load/displacement data during loading and unloading for a polycrystalline ceramic material using a Vickers pyramidal indenter.

Yttria-tetragonal zirconia polycrystalline material was selected as sample 28 and mounted on a stage surface 26 of fixture 24 as illustrated in the figures. Brackets 30 were applied and the sample was firmly fastened to the stage via engagement of bolts 64 into fixture 24. A diamond Vickers pyramidal indenter was selected. The ceramic sample had a top surface 32, facing the indenter, which had been finely polished. A loading rate of about 5 μm per second was applied to the sample up to approximately 1 N. The sample was unloaded at a rate of about 2 μm per minute. The resultant plot of load versus displacement appears in FIG. 16. Calculation of Young's modulus (E) was obtained using equation 3.

In this case $h_{max}$ equals 1.55 μm and dP/dh is 1.34 N/μm. From these measurements, the value of E was estimated to be 187 GPa, which compares well with the known value of 200 GPa for this material.

Example 2
Measurement and Calculation of Strain Hardening Exponent (n) of Nickel (Spherical Indenter).

Figure 17:
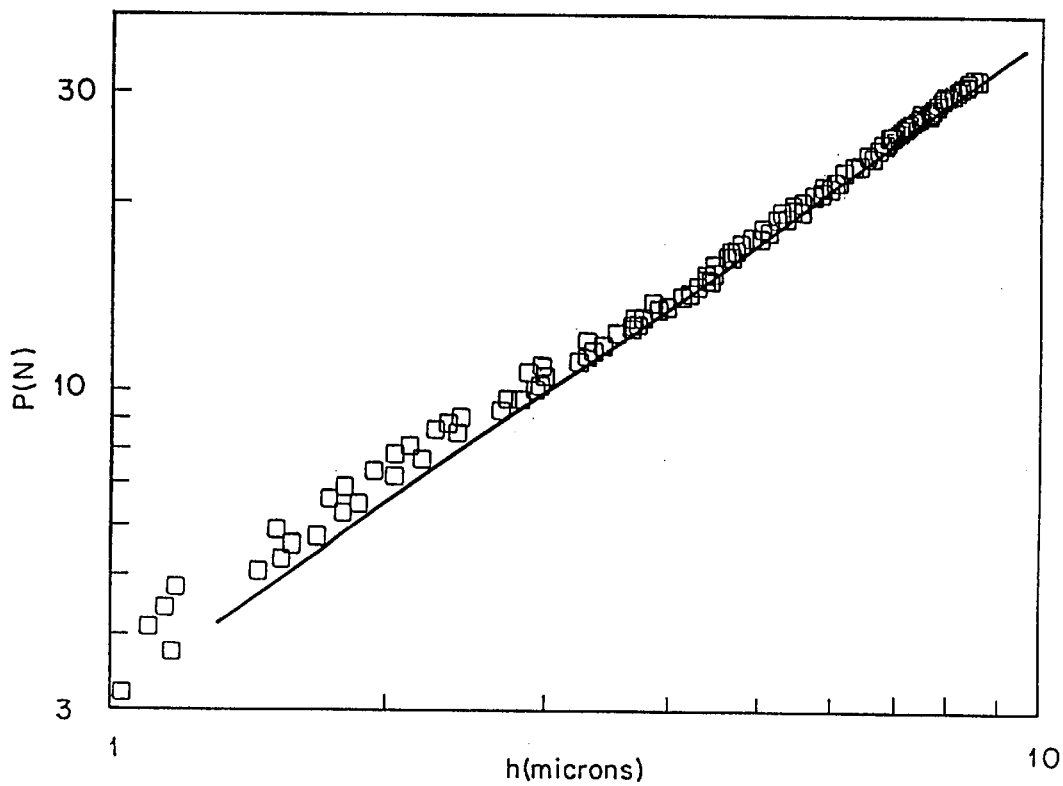
FIG. 17 is a logarithmic plot of experimentally-measured load/displacement of nickel using a spherical indenter.

A load/indentation test of a polished nickel sample with a WC blunt indenter of 1.587 mm diameter, Young's modulus 610 GPa, hardness of 17 GPa, and Poisson ratio of 0.3 was carried out. To calculate hardness exponent (n) the inventive formulation of Equation 12 was used. A plot of log P versus log h became a straight line (for h>3 μm) in the fully plastic regime as shown in FIG. 17. Using this data, n was determined to be 0.19. This result is in good agreement with the value of 0.21 obtained for pure nickel using tensile tests.

Example 3
Evaluation of Yield Strength of Nickel With Spherical Indenter

Experimentation was carried out as in example 1 but using the spherical indenter of example 2. Mean value of $P_{av}$ was 0.73 GPa according to equation 8. Equation 15 gave yield strength of 153 MPa which is in very good agreement with tensile tests where yield strength was measured to be 148 MPa.

Figure 18:
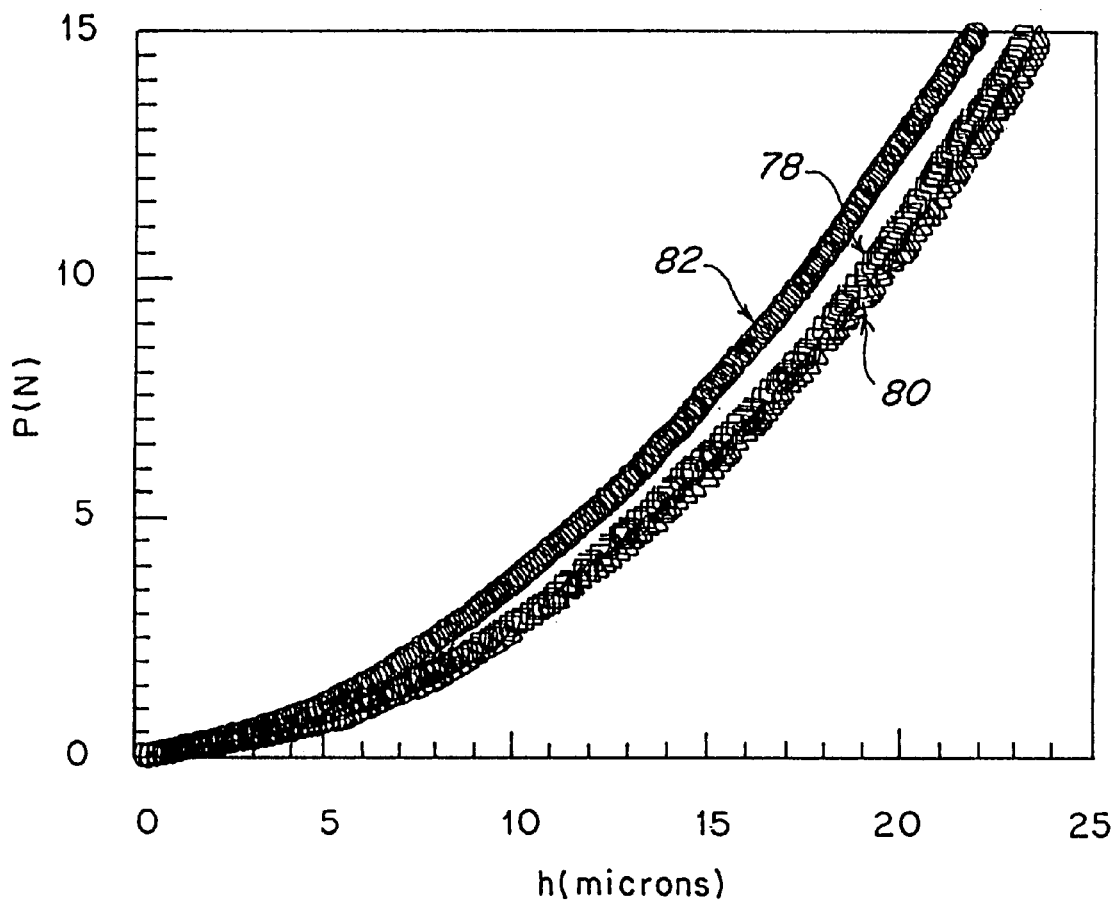
FIG. 18 illustrates experimentally-measured load/displacement data for loading of nickel using a Vickers pyramidal indenter, and comparison with a curve derived theoretically in accordance with the invention.

Example 4
Assessment of the Loading Portion of the Load/Depth Response of Vickers Indentation on a Nickel Sample Experimentation was carried out as in example 1. From Examples 2 and 3, the yield strength and elastic modulus were computed according to the theory of the spherical indentation. Equation 6 then was used to provide the theoretical load/depth curve 78 of FIG. 18. Curves 80 and 82 represent the boundaries of all experimental data, representing ten experiments on Nickel using a Vickers indenter. The theoretical curve falls well within the bounds of experimentation.

Those skilled in the art would readily appreciate that all parameters listed herein are meant to be exemplary and the actual parameters will depend upon the specific application for which the methods and apparatus of the present invention are being used. It is, therefore, to be understood that the foregoing embodiments are presented by way of example only and that, within the scope of the appended claims and equivalents thereto, the invention may be practiced otherwise than is specifically described.

What is claimed is:

1. A computer system for computing an area of contact between an indenter and a surface of a sample to which a load is applied via the indenter, comprising:

input means for receiving signals indicative of a load applied to a sample surface via an indenter and indicative of a depth of penetration of the indenter into the sample; and means for computing maximum contact area between the indenter and the sample surface using the signals received by the input means, where said means for computing computes said contact area from signals received from a single load/unload cycle.

2. A computer system as in claim 1, further comprising means for computing combined Young's modulus of the indenter and the sample, and means for computing Young's modulus of the sample.

3. A computer system as in claim 1, further comprising means for computing hardness of the sample.

4. A computer system as in claim 1, further comprising means for computing yield strength of the sample.

5. A computer system as in claim 4, further comprising means for computing strain hardening exponent of the sample.

6. A computer system as in claim 1, wherein the input means is a computer memory.

7. A computer system as in claim 1, wherein the input means is connected to a computer memory.

8. A computer system as in claim 1, wherein said maximum contacted area computed by the computing means includes any effects of pile-up and sinking-in of a sample material during penetration of the indenter into the sample.

9. A computer system for computing an area of contact between an indenter and a surface of a sample to which a load is applied via the indenter, comprising:

an acquisition module having an input for receiving values of load applied to a sample surface via an indenter and depth of penetration of the indenter into the sample and an output; and an analysis module having an input for receiving said values of load and depth from the output of the acquisition module, and an output providing a signal indicative of maximum contact area between the indenter and the sample surface, where said analysis module accounts for any effects of pile-up and sinking-in of a sample material during penetration of the indenter into the sample in providing the output signal indicative of maximum contact area.

10. A computer system as recited in claim 9, the analysis module further comprising an output providing a signal indicative of Young's modulus of the sample.

11. A computer system as recited in claim 9, the analysis module further comprising an output providing a signal indicative of hardness of the sample.

12. A computer system as recited in claim 9, the analysis module further comprising an output providing a signal indicative of yield strength of the sample.

13. A computer system as recited in claim 12, the analysis module further comprising an output providing a signal indicative of strain hardening exponent of the sample.

14. A computer system as in claim 9, wherein said analysis module can compute said contact area from values of load and depth received from the acquisition module for a single load/unload cycle.

15. A computer system for computing an area of contact between an indenter and a surface of a sample to which a load is applied via the indenter, comprising:

input means for receiving signals indicative of a load applied to a sample surface via an indenter and indicative of a depth of penetration of the indenter into the sample; and means for computing maximum contact area between the indenter and the sample surface, said means for computing maximum contact area including means for accounting for any effects of pile-up and sinking-in of a sample material during penetration of the indenter into the sample, using the signals received by the input means.

16. A computer system as in claim 15, wherein said means for computing maximum contact area computes said contact area from signals received from a single load/unload cycle.

17. A computer system for computing an area of contact between an indenter and a surface of a sample to which a load is applied via the indenter, comprising:

an acquisition module having an input for receiving values of load applied to a sample surface via an indenter and depth of penetration of the indenter into the sample and an output; and an analysis module having an input for receiving said values of load and depth from the output of the acquisition module, and an output providing a signal indicative of maximum contact area between the indenter and the sample surface, where said analysis module computes said contact area from values of load and depth received from the acquisition module for a single load/unload cycle.

18. A computer system as in claim 17, wherein said maximum contact area includes any effects of pile-up and sinking-in of a sample material during penetration of the indenter into the sample.

\* \* \* \* \*